US012729250B2

(12) United States Patent
Kargapolov et al.

(10) Patent No.: US 12,729,250 B2
(45) Date of Patent: Sep. 8, 2026

(54) METHOD OF SYNTHESIS OF CHITOSAN DERIVATIVES AND USES THEREOF

(71) Applicant: NOVOCHIZOL SA, Monthey (CH)

(72) Inventors: Yuriy Kargapolov, Novosibirsk (RU); Vladislav Fomenko, Novosibirsk (RU)

(73) Assignee: NOVOCHIZOL SA, Monthey (CH)

( * ) Notice: Subject to any disclaimer, the term of this patent is extended or adjusted under 35 U.S.C. 154(b) by 778 days.

(21) Appl. No.: 17/798,583

(22) PCT Filed: Feb. 10, 2021

(86) PCT No.: PCT/EP2021/053204

§ 371 (c)(1), (2) Date: Aug. 10, 2022

(87) PCT Pub. No.: WO2021/160667

PCT Pub. Date: Aug. 19, 2021

(65) Prior Publication Data

US 2023/0096466 A1 Mar. 30, 2023

(30) Foreign Application Priority Data

Feb. 11, 2020 (EP) .................................... 20156732
Feb. 11, 2020 (RU) ................................ 2020106398

(51) Int. Cl.

| | |
|---|---|
| ***A01N 43/16*** | (2006.01) |
| ***A61K 8/73*** | (2006.01) |
| ***A61K 9/51*** | (2006.01) |
| ***A61L 15/28*** | (2006.01) |
| ***A61L 27/20*** | (2006.01) |
| ***A61Q 19/00*** | (2006.01) |
| ***C08B 37/08*** | (2006.01) |
| ***C08J 3/24*** | (2006.01) |
| ***C12N 5/00*** | (2006.01) |

(52) U.S. Cl.

CPC ............ *C08B 37/003* (2013.01); *A01N 43/16* (2013.01); *A61K 8/736* (2013.01); *A61K 9/5161* (2013.01); *A61K 9/5192* (2013.01); *A61L 15/28* (2013.01); *A61L 27/20* (2013.01); *A61Q 19/00* (2013.01); *C08J 3/24* (2013.01); *C12N 5/0018* (2013.01); *C08J 2305/08* (2013.01); *C12N 2500/34* (2013.01)

(58) Field of Classification Search

CPC ...... C08B 37/003; A01N 43/16; A61K 8/736; A61K 9/5161; A61K 9/5192; A61L 15/28; A61L 27/20; A61Q 19/00; C08J 3/24; C08J 2305/08; C12N 5/0018; C12N 2500/34

See application file for complete search history.

(56) References Cited

U.S. PATENT DOCUMENTS

| | | | |
|---|---|---|---|
| 5,770,712 | A | 6/1998 | Roy et al. |
| 2014/0017329 | A1 | 1/2014 | Mousa |

FOREIGN PATENT DOCUMENTS

| | | |
|---|---|---|
| JP | 2004-002511 | 1/2004 |
| JP | 2004-211101 | 7/2004 |
| WO | WO 95/15343 | 6/1995 |
| WO | WO 2019/060740 | 3/2019 |

OTHER PUBLICATIONS

Yu, Y., et al. (2008) Synthesis and characterization of thermoresponsive hydrogels cross-linked with chitosan. Cent. eur. j. chem. 6, 107-113 (Year: 2008).*

Pourjavadi, A., et al. (2006). Superabsorbency, pH-Sensitivity and Swelling Kinetics of Partially Hydrolyzed Chitosan-g-poly(Acrylamide) Hydrogels, Turkish Journal of Chemistry, 30(5), Article 7, p. 595-608. (Year: 2006).*

Hastuti, B., et al. (2016), IOP Conf. Ser.: Mater. Sci. Eng. 107, 012020, p. 1-9 (Year: 2016).*

Kim, M.S., et al. (2007), Synthesis and characterization of in situ chitosan-based hydrogel via grafting of carboxyethyl acrylate. J Biomed Mater Res A. 83(3), p. 674-682 (Year: 2007).*

Lal Kashyap, P., et al. (2015). Chitosan nanoparticle based delivery systems for sustainable agriculture, International Journal of Biological Macromolecules, 77, p. 36-51 (Year: 2015).*

Chellathurai, M. S., et al. (2024). Pharmaceutical chitosan hydrogels: A review on its design and applications, International Journal of Biological Macromolecules, vol. 280, Part 2. (Year: 2024).*

Boissier, M.C., et al. (2020) Origins of rheumatoid arthritis, Joint Bone Spine, 87(4), p. 301-306 (Year: 2020).*

Phelps, E.A., et al (2012), Maleimide cross-linked bioactive PEG hydrogel exhibits improved reaction kinetics and cross-linking for cell encapsulation and in situ delivery. Adv Mater. 24(1):64-70 (Year: 2012).*

Phelps, E.A., et al (2012), Maleimide cross-linked bioactive PEG hydrogel exhibits improved reaction kinetics and cross-linking for cell encapsulation and in situ delivery. Adv Mater. 24(1):64-70 (Supplemental) (Year: 2012).*

Anderson, G. W. et al. "N-Hydroxysuccinimide Esters in Peptide Synthesis" *Communications to the Editor*, Oct. 5, 1963, p. 3039.

(Continued)

*Primary Examiner* — Sue X Liu

*Assistant Examiner* — Susannah S Armstrong

(74) *Attorney, Agent, or Firm* — SALIWANCHIK, LLOYD & EISENSCHENK

(57) ABSTRACT

The present invention is directed to a new cross-linked chitosan, preparations, compositions and uses thereof. In particular, the invention relates to nanoparticles and compositions thereof useful as active agents and delivery systems for at least one bioactive agent.

23 Claims, 13 Drawing Sheets

(56) References Cited

OTHER PUBLICATIONS

Arens, J. F. "The Chemistry of Acetylenic Ethers XI. Preparation of acetylenic ethers from aldehydes" *Recueil*, 1955, pp. 271-276, vol. 74.
Belleau, B. et al. "A New Convenient Reagent for Peptide Syntheses" *Journal of the American Chemical Society*, Mar. 13, 1968, pp. 1651-1652, vol. 90, No. 6.
Bhattarai, N. et al. "Chitosan-based hydrogels for controlled, localized drug delivery" *Advanced Drug Delivery Reviews*, Sep. 30, 2009, vol. 62, pp. 83-99.
Bieback, K. et al. "Clinical Protocols for the Isolation and Expansion of Mesenchymal Stromal Cells" *Transfusion Medicine and Hemotherapy*, Jul. 17, 2008, pp. 286-294, vol. 35.
Boccaccini, A. R. et al. "Electrophoretic deposition of biomaterials" *Journal of the Royal Society*, May 26, 2010, pp. S581-S613, vol. 7, doi: 10.1098/rsif.2010.0156.focus.
Brugnerotto, J. et al. "An infrared investigation in relation with chitin and chitosan characterization" *Polymer*, 2001, pp. 3569-3580, vol. 42.
Bu, H. et al. "Synthesis of a hemoglobin-conjugated triblock copolymer for oxygen carrying and specific recognition of cancer cells" *RSC Advances*, 2017, vol. 7, pp. 48166-48175.
Chuan, D. et al. "Chitosan for gene delivery: Methods for improvement and applications" *Advances in Colloid and Interface Science*, Feb. 6, 2019, pp. 1-69, https://doi.org/10.1016/j.cis.2019.03.007.
Ciuffreda, M. C. et al. "Protocols for in vitro Differentiation of Human Mesenchymal Stem Cells into Osteogenic, Chondrogenic and Adipogenic Lineages" Massimiliano Gnecchi (ed.), Chapter 8, *Mesenchymal Stem Cells: Methods and Protocols*, Methods in Molecular Biology, DOI 10.1007/978-1-4939-3584-0_8, Springer Science+Business Media, New York, 2016, pp. 149-158.
Diago-Meseguer, J. et al. "A New Reagent for Activating Carboxyl Groups; Preparation and Reactions of N,N-Bis[2-oxo-3-oxazolidinyl]phosphorodiamidic Chloride" *Synthesis*, Jul. 1980, pp. 547-551 and p. 1091.
Duarte, A. R. C. et al. "Supercritical fluid impregnation of a biocompatible polymer for ophthalmic drug delivery" *The Journal of Supercritical Fluids*, 2007, pp. 373-377, vol. 42.
El-Sherbiny, I. M. "Synthesis, characterization and metal uptake capacity of a new carboxymethyl chitosan derivative" *European Polymer Journal*, Jan. 1, 2009 (available online Nov. 7, 2008), pp. 199-210, vol. 45, No. 1.
Fujino, M. et al. "A New Procedure for the Pentachlorophenylation of N-Protected Amino Acids" *Chem. Pharm. Bull.*, 1968, pp. 929-932, vol. 16, No. 5.
Glazunov, V. P. et al. "A spectrophotometric Determination of the Amino Group Content in Chitosan" *Russian Journal of Bioorganic Chemistry*, 1999, pp. 216-219, vol. 25, No. 3.
Górecka, A. et al. "Diethyl Phosphorobromidate—An Effective New Peptide-Forming Agent" *Synthesis*, Jun. 1978, pp. 474-476, No. 6.
Grant, S. A. et al. "Gold Nanoparticle-Collagen Gels for Soft Tissue Augmentation" *Tissue Engineering Part A*, Epub Mar. 20, 2018, vol. 24, Nos. 13-14, pp. 1-27.
Gudkov, A. T. et al. "Synthesis of pentafluorophenyl esters of amino acids and peptides using pentafluorophenyl trichloroacetate" 1978, vol. 48, No. 9, p. 2146.
Honzl, J. et al. "Amino-Acids and Peptides. XXXIII. Nitrosyl Chloride and Butyl Nitrite as Reagents in Peptide Synthesis by the Azide Method; Suppression of Amide Formation" *Collection Czechoslov. Chem. Commum.*, 1961, pp. 2333-2344, vol. 26.
Hu, H.-B. et al. "Isolation, purification, characterization and antioxidant activity of polysaccharides from the stem barks of *Acanthopanax leucorrhizus" Carbohydrate Polymers*, 2018, pp. 359-367, vol. 196.
Jakubke, H.-D. et al. "Untersuchungen über die peptidchemische Verwendbarkeit von Acelyaminosauer-chinolyl-(8)-estern" *A. Chem. Ber.*, 1966, pp. 2419-2429, vol. 99, No. 8.
Jiang, H.-L. et al. "Chemical Modification of Chitosan as a Gene Transporter" *Current Organic Chemistry*, 2018, pp. 668-689, vol. 22.
Kang, S. et al. "Comparison of pH-sensitive degradability of maleic acid amide derivatives" *Bioorganic & Medicinal Chemistry Letters*, Mar. 26, 2014, pp. 2364-2367, vol. 24.
König, W. et al. "Eine neue Methode zur Synthese von Peptiden: Aktivierung der Carboxylgruppe mit Dicyclohexylcarbodiimid unter Zustaz von 1-Hydroxy-benzotriazolen" *Chem Ber.*, 1970, pp. 788-798, vol. 103.
Kritchenkov, A. S. et al. "Chitosan and its derivatives: vectors in gene therapy" *Russ. Chem. Rev.*, 2017, pp. 231-239, vol. 86, No. 3.
Kubota, N. et al. "A simple preparation of half N-acetylated chitosan highly soluble in water and aqueous organic solvents" *Carbohydrate Research*, 2000, pp. 268-274, vol. 324.
Layek, B. et al. "Chitosan for DNA and gene therapy" J. Amber Jennigs et al. (ed.), Chapter 8, *Chitosan Based Biomaterials, vol. 2: Tissue Engineering and Therapeutics*, Woodhead Publishing, No. 123, 2016, pp. 209-244.
Leplawy, M. T. et al. "Peptides-XI, Synthesis of Peptides Derived From Alpha-Methylalanine" *Tetrahedron*, 1960, pp. 39-51, vol. 11.
Li, B. et al. "Hydrosoluble, UV-crosslinkable and injectable chitosan for patterned cell-laden microgel and rapid transdermal curing hydrogel in vivo" *Acta Biomaterialia*, available online Apr. 25, 2015, pp. 59-69, vol. 22, No. 7.
Li, B. et al. "Ultraviolet-Crosslinkable and Injectable Chitosan/Hydroxyapatite Hybrid Hydrogel for Critical Size Calvarial Defect Repair In Vivo" *Journal of Nanotechnology in Engineering and Medicine*, Nov. 2015 (published online Apr. 8, 2016), pp. 041001-1-041001-6, vol. 6, No. 4.
Li, J. et al. "Development of a mass spectrometry method for the characterization of a series of chitosan" *International Journal of Biological Macromolecules*, Sep. 30, 2018, pp. 89-96, vol. 121.
Lipovka, A. et al. "The Effect of Adding Modified Chitosan on the Strength Properties of Bacterial Cellulose for Clinical Applications" *Polymers*, 2021, pp. 1-17, vol. 13.
Losse, G. et al. "Synthetische Peptide ALS Hydrolasemodelle" *Ann. Chem.*, 1964, pp. 148-159, No. 678.
Losse, G. et al. "Neue Möglichkeitzen zur Knüpfung der Peptidbindung" *Ann. Chem.*, 1960, pp. 144-149, No. 636.
Mao, S. et al. "Chitosan-based formulations for delivery of DNA and siRNA" *Advanced Drug Delivery Reviews*, Sep. 29, 2009, pp. 12-27, vol. 62.
Nefkens, G. H. L. et al. "A Novel Activated Ester in Peptide Syntheses" *Amer. Chem. Soc.*, Mar. 5, 1961, p. 1263, vol. 83, No. 5.
Paul, R. et al. "N,N'-Carbonyldiimidazole, a New Peptide Forming Reagent" *J. Amer. Chem. Soc.*, Sep. 5, 1960, pp. 4596-4600, vol. 82, No. 17.
Pishbin, F. et al. "Single-step electrochemical deposition of antimicrobial orthopaedic coatings based on a bioactive glass/chitosan/nano-silver composite system" *Acta Biomaterialia*, Mar. 16, 2013, pp. 7469-7479, vol. 9.
Sakakibara, S. et al. "The Trifluoroacetate Method of Peptide Synthesis. I. The Synthesis and Use of Trifluoroacetate Reagents" *Bull. Chem. Soc. Jap.*, Nov. 1965, pp. 1979-1984, vol. 38, No. 1.
Sánchez, A. et al. "Esterification of Maleamic Acids without Double Bond Isomerization" *Eur. J. Org. Chem.*, Mar. 27, 2010, pp. 2600-2606.
Schwyzer, R. et al. "9. Über aktivierte Ester. II. Synthese aktivierter Ester von Aminosäuer-Derivaten" *Helvetica Chimica Acta*, 1955, pp. 80-83, vol. 38, No. 9.
Stevens, C. L. et al. "Nitrogen Analogs of Ketens. V. Formation of the Peptide Bond" *J. Amer. Soc.*, Aug. 5, 1958, pp. 4069-4071, vol. 80.
Stradleigh, T. W. et al. "Fixation Strategies for Retinal Immunohistochemistry" *Prog. Retin Eye Res.*, Sep. 2015, pp. 1-53, vol. 48.
Takebe, T. et al. "Organoids by design" *Science*, Jun. 7, 2019, pp. 1-13, vol. 364, No. 6444.
Taschner, E. et al. "Darstellung aktiver Pyridyl-(3)-ester N-geschützter Aminosäuren und peptide sowie deren Anwendung zur Peptid-Synthese" *Liebigs Ann. Chem. Bd.*, 1965, pp. 177-181, No. 690.

(56) References Cited

OTHER PUBLICATIONS

Teplyakova, O. I. et al. "Novochizol™ Seed Treatment: Effects on Germination, Growth and Development in Soft spring Wheat" *Nat Prod Chem Res*, 2022, pp. 1-10, vol. 10, No. 5.
Weidner, E. "Impregnation via supercritical $CO_2$—What we know and what we need to know" *J. of Supercritical Fluids*, Dec. 15, 2017, pp. 1-31, https://doi.org/10.1016/j.supflu.2017.12.024.
Wieland, T. et al. "Über Peptid-Synthesen. 3. Mitteilung; Die Verwendung von Anhydriden aus N-acylierten Aminosäuren und Derivaten anorganischer Säuren" *Ann. Chem.*, 1951, pp. 190-194, vol. 572, No. 3.
Woodward, R. B. et al. "A New Synthesis of Peptides" *J. Amer. Chem. Soc.*, Feb. 20, 1961, pp. 1010-1012, vol. 83, No. 4.
Xuan, S. et al. "Synthesis and Characterization of Well-defined PEGylated Polypeptoids as Protein-resistant Polymers" *Biomacromolecules*, Feb. 6, 2017, cover page and pp. 1-40, vol. 1, No. 3.
Zhao, H. et al. "Improved Biolistic Transfection of Hair Cells" *PLoS One*, Oct. 1, 2012, pp. 1-8, vol. 7, Issue 10, e46765.
Zilkha, A. et al. "Preparation of Aspartyl Amides and Peptides via N-Benzyl-DL-aspartic Anhydride Hydrochloride" *Journal of the Chemical Society*, May 16, 1957, pp. 4397-4399.
Written Opinion in International Application No. PCT/EP2021/053204, May 18, 2021, pp. 1-10.

* cited by examiner

A

B1

B2

B3

B4 nm
140
0
4,0
2,0
μm
0
0
2,5
5,0
μm

A

B

A

A 75 25 93,8 93,8
89,6 10,4 93,8 97,9
97,9 2,1 100 100

Control (no treatment)
0.1%
0.05%

% radicle emergence (after 1 day)
% absence of radicle emergence (after 1 day)
% germination energy, after 3 days
% germination capacity, after 7 days

METHOD OF SYNTHESIS OF CHITOSAN DERIVATIVES AND USES THEREOF

CROSS-REFERENCE TO RELATED APPLICATION

This application is the U.S. national stage application of International Patent Application No. PCT/EP2021/053204, filed Feb. 10, 2021.

FIELD OF THE INVENTION

The present invention relates to the preparation of chitosan, in particular nanoparticles from chitosan, preparations, compositions and uses thereof, in particular in the fields of chemistry, biology, medicine and material sciences.

BACKGROUND OF THE INVENTION

Biopolymers are promising materials as carriers of various drugs and other active substances due to their biocompatibility, biodegradation, and non-toxicity when administered. With suitable chemical modification, these polymers can provide better materials for drug delivery systems, where active substances can be both low molecular weight compounds (small molecules) or high molecular weight compounds (marcomolecules). Nanostructured drug carriers allow the delivery of high-molecular compounds such as nucleic acids and proteins (*Advances in Polymer Science. Chitosan for Biomaterials I. Volume Editors*: R. Jayakumar, M Prabaharan, R. A. A. Muzzarelli. Springer Heidelberg Dordrecht London New York 2011 DOI 10.1007/978-3-642-23114-8).

Chitosan is one of the most promising biopolymer candidates for the creation of nanoparticles. On the one hand, it has attractive native properties such as mucoadhesiveness, biocompatibility and low toxicity, ability to biodegradation and the formation of complexes and the other hand, the high regularity of the structure and the presence of hydroxyl and amino groups in it presents good prospects for selective modification of the polymer.

Therefore, those properties of chitosan have attracted the attention for the development of drug delivery solutions (Bhattarai et al., 2010, *Advanced Drug Delivery Reviews,* 62 83-99. doi: 10.1016/j.addr.2009.07.019).

Although chitosan presents several favourable characteristics as an excellent carrier, the use of unmodified chitosan is limited due to its low solubility in physiological conditions. To overcome this limitation, many different chemical modifications of chitosan have been developed, (Kritchenkov et al., 2017, *Russ. Chem. Rev.,* 86, 231-239. doi.org/10.1070/RCR4636; Chuan et al., 2019, *Adv. Colloid Interface Sci.,* 268, 25-38.; Jiang, H.-L.; Xing et al., 2018, *Curr. Org. Chem.,* 22, 668-689. DOI: 10.2174/1385272821666170926163544; Layek, B.; Singh, J. 8—*Chitosan for DNA and gene therapy. In Chitosan Based Biomaterials Volume* 2; Jennings, J. A., Bumgardner, J. D., Eds.; Woodhead Publishing: Cambridge, UK, 2017; pp. 209-244).

The structure of chitosan offers the possibility to be modified in a variety of ways. To increase hydrophobicity, chitosan amides can be readily made with fatty acids, sterol derivatives, urocanic acid, carboxylic acid derivatives containing an imidazole fragment, etc. Alternatively, secondary chitosan amines can be formed using alkyl substituents of various structures, pyridine derivatives, spermidine and others by alkylation or reductive amination through appropriate Schiff bases. To increase hydrophilicity, chitosan amides may be created with amino acids, including sulfur-containing amino acids, lactobionic acid, thioglycolic acid, etc. Additionally, secondary amines of chitosan may be obtained using various sugars, polyethyleneimine and its derivatives. Synthesis of polyethylene glycol derivatives by pegylation is especially popular. Chitosan derivatives produced according to these methods are enhanced in their capacity to form nanoparticles, in particular with polyelectrolytes such as nucleic acids and may have altered pharmacological properties. (Mao et al., 2010, *Advanced Drug Delivery Reviews,* 62, 12-27 doi:10.1016/j.addr.2009.08.004).

Chitosan nanoparticles may be formed in an essentially irreversible manner through chemical cross-linking that involves the formation of covalent bonds with the use of different reagents for catalyzing such cross-linking (Bhattarai et al., 2010, supra) Historically, glutaraldehyde and formaldehyde were the first and most popular agents used for this cross-linking but those are losing popularity today due to the difficulty of removing all trace of these toxic compounds, as well as the slow hydrolysis of nanoparticles that releases these aldehydes. Genepine has received much attention recently, but this reagent is very expensive and prone itself to polymerization. Diethyl squarate (DES), ethyleneglycol diglycidylether (EGDE) and blocked diisocyanates react rather slowly and the reactions with then take place mainly at elevated temperatures, which can contribute to side reactions. Photo-activated cross-linking reagents also exist: functional azides, functional acrylates, as well as enzyme-activated agents—phloretic acid and activated quinones. For example, Baoqiand et al., 2015 in *Acta Biomaterialia,* 22, 1742-7061 or *Journal of Nanotechnology in engineering and medicine,* 6, 041001-6 provide a method for producing cross-linked chitosan using photo-initiated radical polymerization of a chitosan in solution after reacting the chitosan with methacrylic anhydride, thereby leading to a polyacrylamide compound in the form of a gel or foam. Carboxymethyl derivatives of chitosan are described in El-sherbiny et al., 2009, *European Polymer Journal* 45, 1, 199-210 wherein in a first step a carboxylic group is introduced into chitosan by reacting the primary alcoholic group in chitosan with monochloroacetic acid in an alkaline medium and in a second stage acryloylglycine polymers are added through light-induced polymerization leading to a chitosan without internal cross-linking. U.S. Pat. No. 5,770,712 describes a method a making a cross-linked chitosan by combining chitosan material having unreacted primary amine groups with an excess amount of a polyfunctional epoxide compound having at least two epoxide groups. The cross-linking reaction of chitosan with 1,4-butanediol diglycidyl ether results in amino-ethanol cross-linked derivatives of chitosan which are poorly soluble at physiological pH (7 and higher).

It is also possible to use for cross-linking pre-derivatized chitosan through the formation of Schiff bases with chitosan containing an aldehyde group, the formation of disulfide bridges with chitosan in the previously functionalized by reagents with terminal sulfhydryl group and the addition of Michael with chitosan previously treated with functional acrylates in the presence of a weak base.

All of these methods involve the formation of nanoparticles when chitosan is in solution. In some cases, all chemical reactions are driven to completion in the liquid phase, in others, they are completed at a later stage, for example during or after spray drying or lyophilization. Importantly, in all cases, the process is initiated and its key stages take place with chitosan that is in a dissolved state (Jayakumar et al., 2011, supra). The need for chitosan to be dissolved imposes significant constraints on the synthesis of the nanoparticles. This owes to the fact that chitosan is only water soluble in the form of salts in the presence of acids. In this form, there is an anomalous increase in viscosity with increasing concentrations for any solution above 2% chitosan, a number which imposes significant restrictions on the possible implementation of the synthesis, as well as on the possibility of high throughput from the reaction apparatus. In particular, wall-effects when mixing a viscous solution can create significant heterogeneity of the concentrations of reagents in the reaction vessel and, as a consequence, heterogeneity in the nanoparticles' properties. Another complication is that high-nucleophilic amino groups are most often used for cross-linking, but in solution they should be ionized to keep chitosan in a dissolved state.

Thus, there is a need to develop new routes of synthesis for the formation of chitosan nanoparticles in an efficient and cost-effective manner.

SUMMARY OF THE INVENTION

The present invention relates to the unexpected finding of a new method for producing nanoparticles from chitosan which presents the advantage avoiding the need of dissolving the chitosan starting material and therefore having recourse to the formation of salts or the use of diluted acid aqueous solutions or the need to disperse the chitosan in solution and therefore having recourse to emulsification, grinding or other procedures that could have a mechanical impact on the integrity of the polymer. In particular, the invention relates to a new method of cross-linking chitosan, in particular where, through two chemical steps new intra-chemical bonds between different parts of the chitosan molecule are formed. According to a particular aspect, the absence of dissolution of the chitosan leads to a more efficient synthesis turnover rate (e.g. about 2 orders of magnitude over cross-linking methods using dissolved chitosan).

The resulting product spontaneously forms nanoparticles at the end of the second step of the method of preparation, those nanoparticles being suitable for a wide range of applications. Further advantageously, the resulting cross-linked chitosan product has similar biological activities to those of standard linear or branched chitosans but unexpectedly exhibits some particular advantages in terms of stability over a broad range of biologically relevant pH or microbial conditions and physicochemical properties that allows an easier handling.

An aspect of the invention provides a method for the preparation of a cross-linked chitosan according to the invention.

Another aspect, the invention relates to a new cross-linked chitosan, in particular a new cross-linked chitosan which spontaneously forms nanoparticles.

Another aspect of the invention relates to a composition comprising at least one cross-linked chitosan according to the invention and at least one carrier.

Another aspect of the invention relates to a pharmaceutical composition comprising at least one cross-linked chitosan according to the invention and at least one pharmaceutically acceptable carrier.

Another aspect of the invention relates to nanoparticles comprising one cross-linked chitosan according to the invention.

Another aspect of the invention relates to a cosmetic composition comprising at least one cross-linked chitosan according to the invention.

Another aspect of the invention relates to a soft tissue filler comprising at least one cross-linked chitosan according to the invention or a composition thereof according to the invention.

Another aspect of the invention relates to a wound dressing comprising at least one cross-linked chitosan according to the invention.

According to another particular embodiment, is provided a reconstruction tissue comprising at least one cross-linked chitosan or a composition thereof according to the invention.

Another aspect of the invention relates to an agricultural composition comprising at least one cross-linked chitosan according to the invention.

Another aspect of the invention relates to a method of preparation of a composition (e.g. such as a soft tissue filler, a wound dressing or a reconstruction tissue) comprising at least one cross-linked chitosan or nanoparticles thereof according to the invention.

Another aspect of the invention relates to cross-linked chitosan according to the invention for use in in vivo drug delivery, in vitro cell or biological tissue culture and tissue engineering applications.

According to another particular embodiment, is provided a cell or biological tissue culture medium comprising at least one cross-linked chitosan or a composition thereof according to the invention.

Another aspect of the invention relates to a cross-linked chitosan according to the invention for use in the prevention and/or treatment of a medical disorder and in particular cardiovascular conditions, such as cardiac arrhythmias, in particular atrial fibrillation and hypertension, joint pathologies and articular diseases, such as rheumatoid arthritis, osteoarthritis, spondyloarthritis, and traumatic events leading to cartilage, bone, ligament or synovial capsule damage, eye pathologies and injuries, such as dry eye syndrome, uveitis, glaucoma, corneal lesions, connective tissue disorders, such as lupus and polymyositis, skin/mucous membrane disorders or injuries, such as wounds, scars, psoriasis, acne, eczema, rosacea, burns of physical or chemical nature, in particular surgical wounds and sunburns, ulcers, haemorrhoids, periodontal and dental diseases, dural damage such as following accidental injury or brain and central nervous system surgery, malignant and benign neoplasms, in particular carcinomas, sarcomas, lymphomas, and melanomas, postoperative complications such as fistulas and infections, tumors or vascular malformations.

Another aspect of the invention relates to a use of a cross-linked chitosan according to the invention for the preparation of a pharmaceutical formulation for the prevention and/or treatment of a medical disorder and in particular cardiovascular conditions, such as cardiac arrhythmias, in particular atrial fibrillation and hypertension, joint pathologies and articular diseases, such as rheumatoid arthritis, osteoarthritis, spondyloarthritis, and traumatic events leading to cartilage, bone, ligament or synovial capsule damage, eye pathologies and injuries, such as dry eye syndrome, uveitis, glaucoma, corneal lesions, connective tissue disorders, such as lupus and polymyositis, skin/mucous membrane disorders or injuries, such as wounds, scars, psoriasis, acne, eczema, rosacea, burns of physical or chemical nature, in particular surgical wounds and sunburns, ulcers, haemorrhoids, periodontal and dental diseases, dural damage such as following accidental injury or brain and central nervous system surgery, malignant and benign neoplasms, in particular carcinomas, sarcomas, lymphomas, and melanomas, postoperative complications such as fistulas and infections, tumors or vascular malformations.

Another aspect of the invention relates to a use of cross-linked chitosan according to the invention for the preparation of a cell or biological culture medium or of a reconstruction tissue.

Another aspect of the invention relates to a method for the preparation of a drug delivery system for a bioactive agent.

According to another particular embodiment, is provided a method for identifying a cross-linked chitosan obtainable from a method according to the invention.

Another aspect of the invention relates to a method of preventing, treating or ameliorating a medical disorder, and in particular cardiovascular conditions, such as cardiac arrhythmias, in particular atrial fibrillation and hypertension, joint pathologies and articular diseases, such as rheumatoid arthritis, osteoarthritis, spondyloarthritis, and traumatic events leading to cartilage, bone, ligament or synovial capsule damage, eye pathologies and injuries, such as dry eye syndrome, uveitis, glaucoma, corneal lesions, connective tissue disorders, such as lupus and polymyositis, skin/mucous membrane disorders or injuries, such as wounds, scars, psoriasis, acne, eczema, rosacea, burns of physical or chemical nature, in particular surgical wounds and sunburns, ulcers, haemorrhoids, periodontal and dental diseases, dural damage such as following accidental injury or brain and central nervous system surgery, malignant and benign neoplasms, in particular carcinomas, sarcomas, lymphomas, and melanomas, postoperative complications such as fistulas and infections, tumors or vascular malformations, said method comprising administering to a subject in need thereof an effective amount of at least one cross-linked chitosan according to the invention or a pharmaceutical formulation thereof.

Another aspect of the invention relates to a kit comprising at least one cross-linked chitosan of the invention or composition thereof, e.g. in a lyophilized form.

Another aspect of the invention relates to a kit for preparation of nanoparticles for encapsulation of material, e.g. bioactive agent, drug substance, protein, antibody, saccharide, nucleic acid, or a combination thereof or for prevention or treatment comprising at least one cross-linked chitosan of the invention or composition thereof.

DETAILED DESCRIPTION

Figure 1:
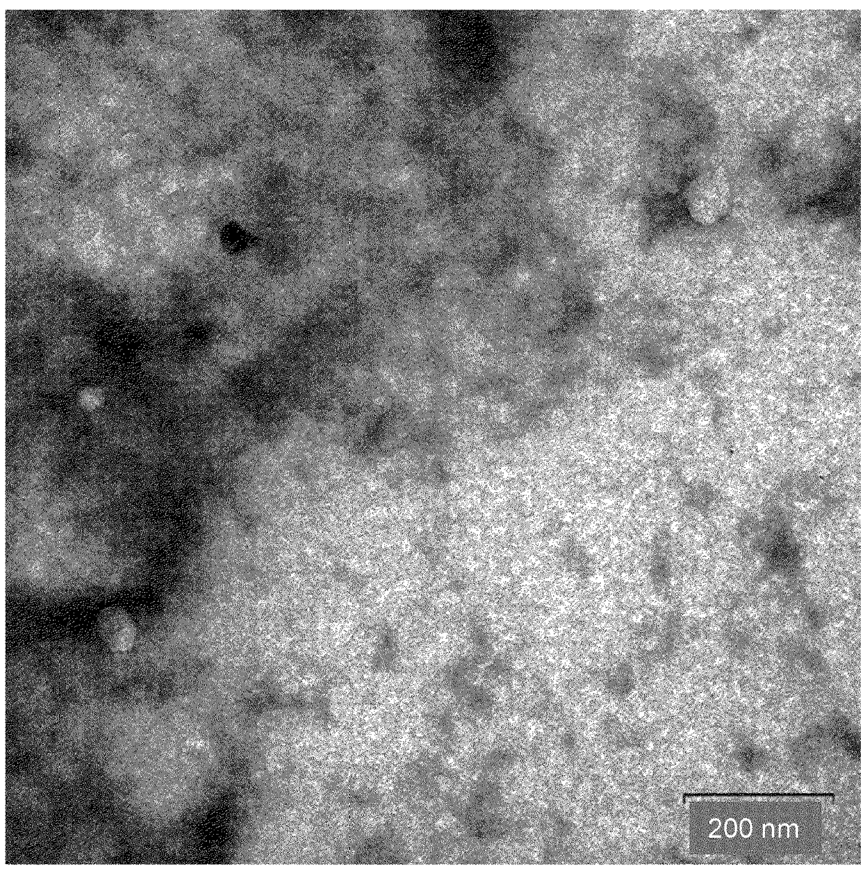
FIG. 1 shows the characterization of cross-linked chitosan nanoparticles of the invention (Example 2i). A: by micrograph of the stained chitosan (3.2% cross-linked 501 kDa chitosan) as described in Example 3; B: Atomic force microscopy of dried films of comparative linear chitosan (B1) and corresponding cross-linked chitosan nanoparticles of the invention (B2), cross-linked chitosan nanoparticles of the invention at high magnification (B3) and low magnification (B4).
Figure 1:
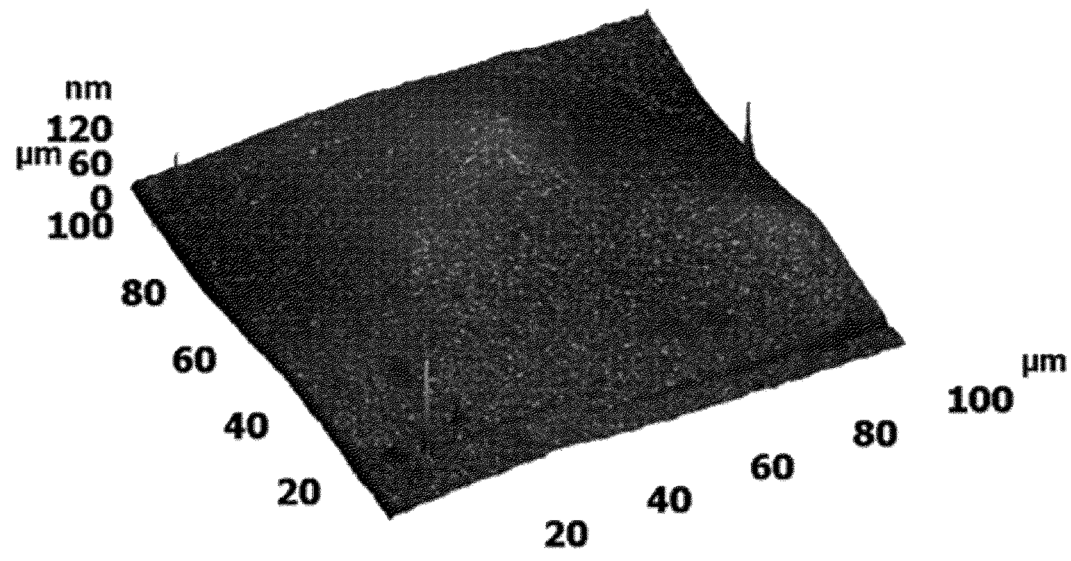
Figure 1:
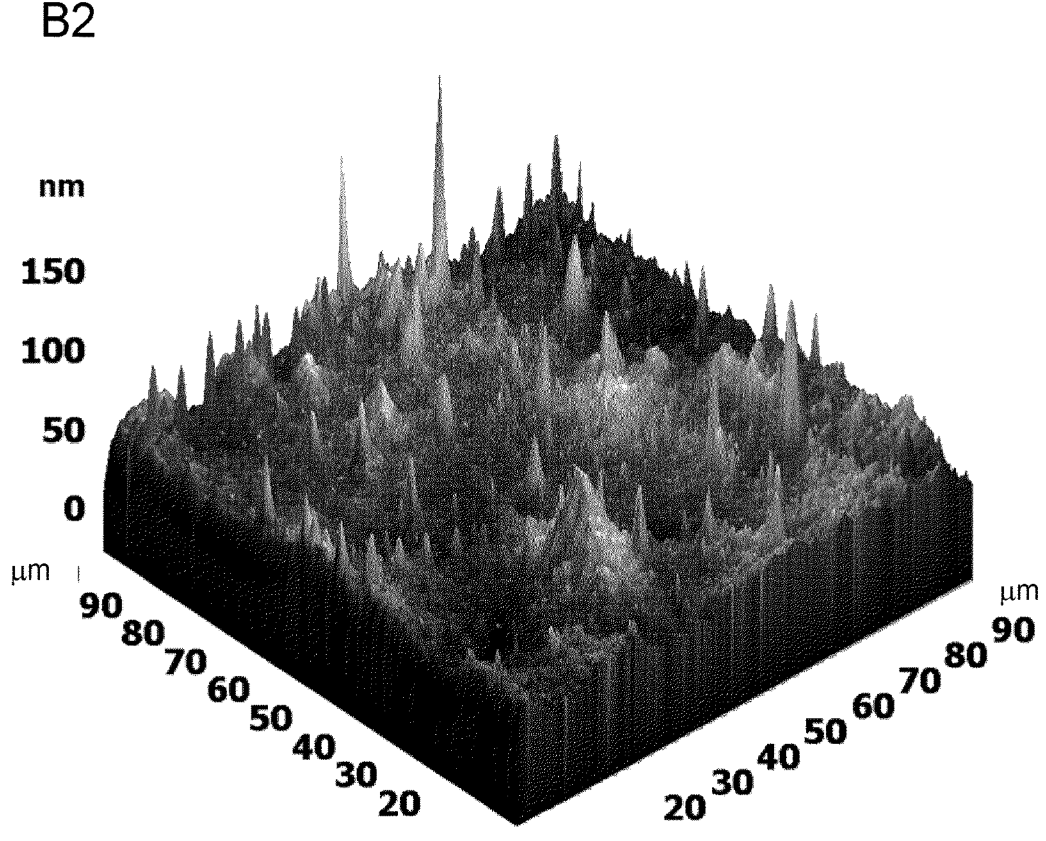
Figure 1:
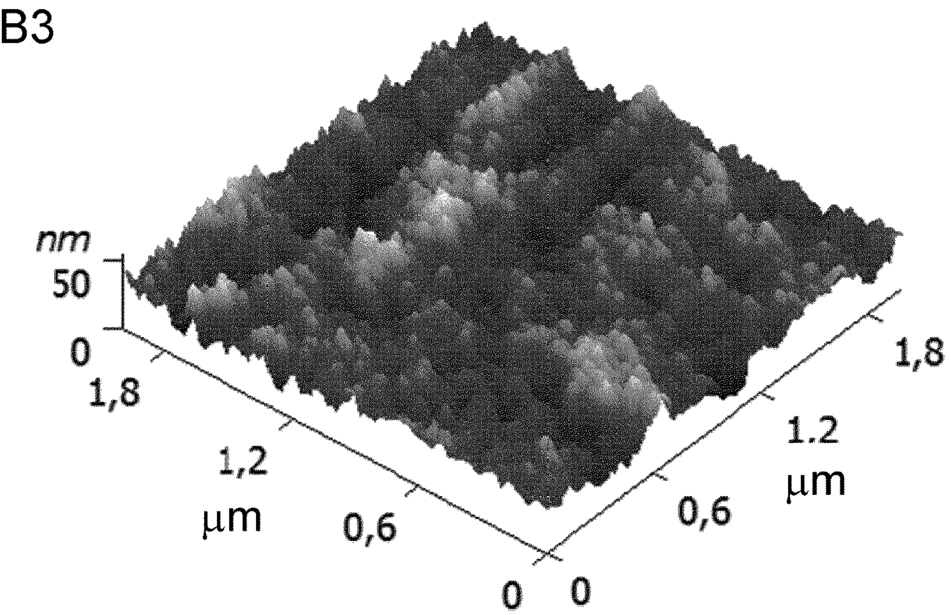
Figure 1:
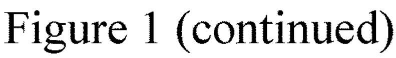

The term "degree of crosslink" as used herein means the quantity functional groups converted into crosslinking or grafting bonds relative to the total quantity of functional groups initially present on the chitosan, expressed as a percentage.

The term "alkyl" when used alone or in combination with other terms, comprises a straight or branched chain of $C_1$-$C_{50}$ alkyl which refers to monovalent alkyl groups having 1 to 50 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refers respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkenyl" when used alone or in combination with other terms, comprises a straight chain or branched $C_2$-$C_{50}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3, 7, 11, 15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH═$CH_2$), n-2-propenyl (allyl, —$CH_2$CH═$CH_2$), isopropenyl, 1-propenyl, 2-methyl propenyl, 1-butenyl, 2-butenyl, and 3-methyl-2-butenyl and the like.

The term "alkynyl" when used alone or in combination with other terms, comprises a straight chain or branched $C_2$-$C_{50}$ alkynyl. It may have any available number of triple bonds in any available positions. This term is exemplified by groups such as alkynyl groups that may have a carbon number of 2-50, and optionally a double bond, such as ethynyl (—C≡CH), 1-propynyl, 2-propynyl (propargyl: —$CH_2$C≡CH), 2-butynyl, 2-pentene-4-ynyl, and the like. Particularly, these include $C_2$-$C_8$ alkynyl, more preferably $C_2$-$C_6$ alkynyl and the like. Preferably those include $C_2$-$C_6$ alkynyl which refers to groups having 2 to 6 carbon atoms and having at least 1 or 2 sites of alkynyl unsaturation.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include azetidinyl, pyrrolidinyl, piperidinyl, piperazinyl, morpholinyl, tetrahydrofuranyl and the like.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "aryl $C_1$-$C_6$ alkyl," "heteroaryl $C_1$-$C_6$ alkyl," "$C_1$-$C_6$ alkyl cycloalkyl," "$C_1$-$C_6$ alkyl heterocycloalkyl," "amino," "aminosulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like. The term "pharmaceutically acceptable" refers to a carrier comprised of a material that is not biologically or otherwise undesirable and not especially toxic.

The term "carrier" refers to any component present in a pharmaceutical formulation other than the active agent and thus includes diluents, binders, lubricants, disintegrants, fillers, coloring agents, wetting or emulsifying agents, pH buffering agents, preservatives and the like.

The term "bioactive agent" is used to describe any agent with biological activity to be incorporated into a graft polymer composition of the invention. It may be natural, synthetic, semi-synthetic or a derivative thereof and may include hydrophobic, hydrophilic, soluble and insoluble compounds. More specifically, it may be any bioactive agent useful for the treatment and/or prevention and/or diagnosis of conditions in any therapeutic area known in mammals, such as animals and humans, particularly humans, which include, but are not limited to cardiac arrhythmias such as atrial fibrillation, hypertension, inflammatory conditions disorders or diseases, in particular autoimmune and non-autoimmune inflammatory conditions, including joint pathologies and articular diseases (such as rheumatoid arthritis, osteoarthritis and spondyloarthritis), eye pathologies (such as dry eye syndrome, uveitis, glaucoma, corneal lesions), connective tissue disorders (such as lupus or polymyositis), skin disorders or injuries (such as wounds, scars, psoriasis, acne, eczema, rosacea, burns of physical or chemical nature, sunburns), periodontal and dental diseases, hemorrhoids, ulcers, diseases amenable to gene therapy, diseases amenable to cell therapy, duraplasty and dural repair following brain and central nervous system surgery, neuroplasty, pain, postoperative fistula and infection, traumatological diseases, benign and malignant neoplasms and infections. The bioactive agents may be selected from a macromolecular compound or a small molecule compound, such as peptides, proteins, oligo- and poly-nucleotides, anti-infectives, antibiotics, antimicrobials, antiviral drugs, antibacterial, antifungal drugs, growth factors, enzymes, antigenes, antitumoral drugs, anti-inflammatory drugs, anaesthetics, antineoplastic drugs, analgesics, anticoagulants, haemostatic drugs, cells and antibodies. The term "inflammatory disorder or disease" refers to all diseases that include inflammation and release or pro-inflammatory cytokines as the main or significant disease mechanism, such as inflammatory bowel disease, allergy, asthma, autoimmune diseases, hepatitis, other organ inflammations and related diseases.

The term "skin disorders" or "skin diseases" includes skin damages where the skin surface presents sore depression without necessarily a cut on its surface such as age-related tissue damages (e.g. wrinkles), wounds and scars such as for example acne or rubella scars. Those disorders further include wounds, scars, psoriasis, acne, eczema and rosacea. The term "wounds", includes any damaged tissue, for example following trauma or surgery. Wounds in mammals include for examples abrasions lacerations, contusions, concussions, stab wounds, skin cuts, surgical wounds, gunshot wounds, thermal wounds, chemical wounds, sunburn, bites and stings and electrical wounds. It further includes chronic skin disorders such as ulcers and other inflammatory skin conditions.

The term "eye pathologies or disorders" are disorders or injuries that affect the eye and in particular the cornea. Such disorders include corneal abrasion, corneal scratches, corneal alkali burns, age-related macular degeneration, bulging eyes, cataracts, cytomegalovirus retinitis, color blindness, strabismus, diabetic macular edema, eye floaters and eye flashes, glaucoma, keratoconus, lazy eye, low vision, ocular hypertension, retinal detachment, eyelid twitching, uveitis, keratoconjunctivitis sicca (KCS) and dry eye syndrome.

The term "articular or joint pathologies" includes osteoarthritis, arthritic pain, rheumatoid arthritis, infection and inflammation pain, traumatic knee events leading to cartilage, traumatic events of the hip joint, bone, ligament or synovial capsule damage.

The term "reconstruction tissue" refers to a biological tissue (endogeneous or exogeneous) or a synthetic or semi-synthetic material useful for repairing damaged tissues of the body such as epidermal, neurological, cartilage or bone tissues as well as for the construction of organoids for biological testing such as described in Takebe et al., 2019, *Science,* 364, 6444, 956-959, DOI: 10.1126/science.aaw756.

As used herein, "treatment" and "treating" and the like generally mean obtaining a desired pharmacological and/or physical and/or physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions such as improvement or remediation of damage.

The term "subject" as used herein refers to mammals. For examples, mammals contemplated by the present invention include human, primates, and domesticated animals such as cattle, sheep, pigs, horses and particularly race horses, laboratory rodents and the like.

The term "efficacy" of a treatment according to the invention can be measured based on changes in the course of disease in response to a use according to the invention. For example, the efficacy of a treatment according to the invention can be measured by disappearance or reduction of clinical signs or symptoms or more favorable measurements of disease biomarkers, such as cytokines, growth factors or other signaling molecules and their receptors, cell surface markers, cell counts and gene expression profiles.

Method of Preparation of a Chitosan According to the Invention and Characterization Thereof According to a particular aspect, is provided a method for the preparation of a cross-linked chitosan comprising the following steps:

a) providing a chitosan and leaving the said chitosan to swell in a solvent;

b) acylating the amino groups of said chitosan with an acrylic compound of Formula (I):

(I)

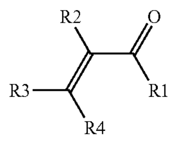

wherein $R_1$ is an a halogen or any other leaving group that upon removal, ensures acylation of an amino group such as 3-hydroxybenzotriazole ester, anhydride (including mixed anhydrides), N-hydroxysuccinimide, pentachlorophenol, 2-nitro-4-sulfophenol esters and other similar leaving groups; $R_2$, $R_3$ and $R_4$ are independently selected from H; optionally substituted alkyl (e.g. $C_1$-$C_6$ alkyl), optionally substituted alkenyl (e.g. $C_2$-$C_6$ alkenyl), optionally substituted alkynyl (e.g. $C_3$-$C_6$ alkynyl), optionally substituted cycloalkyl (e.g. $C_3$-$C_8$-cycloalkyl), optionally substituted cycloalkenyl (e.g. $C_4$-$C_8$ cycloalkenyl), optionally substituted cycloalkynyl (e.g. $C_5$-$C_8$ cycloalkynyl), optionally substituted heterocycloalkyl; optionally substituted aryl (e.g. optionally substituted phenyl), optionally substituted heteroaryl and optionally substituted aryl $C_1$-$C_6$ alkyl, in particular benzyl; wherein the term "substituted refers to groups substituted with from 1 to 5 substituents selected from the group consisting of halogen, —COOR', —NR'R", =O, —OR', —COR', —CONR'R", —SR', $—SO_3R'$, $—SO_2NR'R"$, —SOR', $—SO_2R'$, $—NO_2$, or —CN; or $R_1$ and $R_2$ or $R_1$ and $R_3$, or $R_1$ and $R_4$ together form an optionally substituted 4-24 membered aryl, heteroaryl, cycloalkyl or heterocycloalkyl (e.g. a 6-24 membered aryl, heteroaryl, cycloalkyl or heterocycloalkyl such as an optionally substituted 8-24 membered aryl, heteroaryl, cycloalkyl or heterocycloalkyl);

c) reacting the acylation product of step b) in the presence of a base (Aza-Michael reaction);

d) purifying the cross-linked chitosan obtained from step c) (e.g. from salt impurities and/or aprotic solvent).

According to a particular embodiment, the solvent used under step a) and/or b) is a protic solvent (such as alcohols or water).

According to a particular embodiment, the free acrylic acids which are formed if a protic solvent (such as alcohols or water) is used under step a) and/or b) to conduct the process are washed off from the reaction mixture before carrying out step c).

According to another particular embodiment, the solvent is an aprotic solvent, in particular under step a) and/or b) and/or c).

According to a particular embodiment, if an aprotic solvent is used under step c) if no further step f) of subsequent acylation is carried out.

According to a particular embodiment, step a) is conducted at room temperature.

According to a particular embodiment, the R3 or R4 but also R2 groups of the acylated product of step b) will react with the primary amino groups of the glucosamine backbone to form a cross-link between glucosamines. The groups reacting will depend on the specific acrylic compound. For example, for acrylic and methacrylic acids, the groups reacting with the primary amino groups of the glucosamine backbone are groups R3 or R4. However, when R3 and R4 groups are replaced by halogen atoms, then R2 groups will react with the primary amino groups of the glucosamine backbone.

According to a further particular embodiment, this cross-linking leads to the formation of nanoparticles.

According to particular aspect, the method of the invention can be schematized under Scheme 1 as follows:

Scheme 1

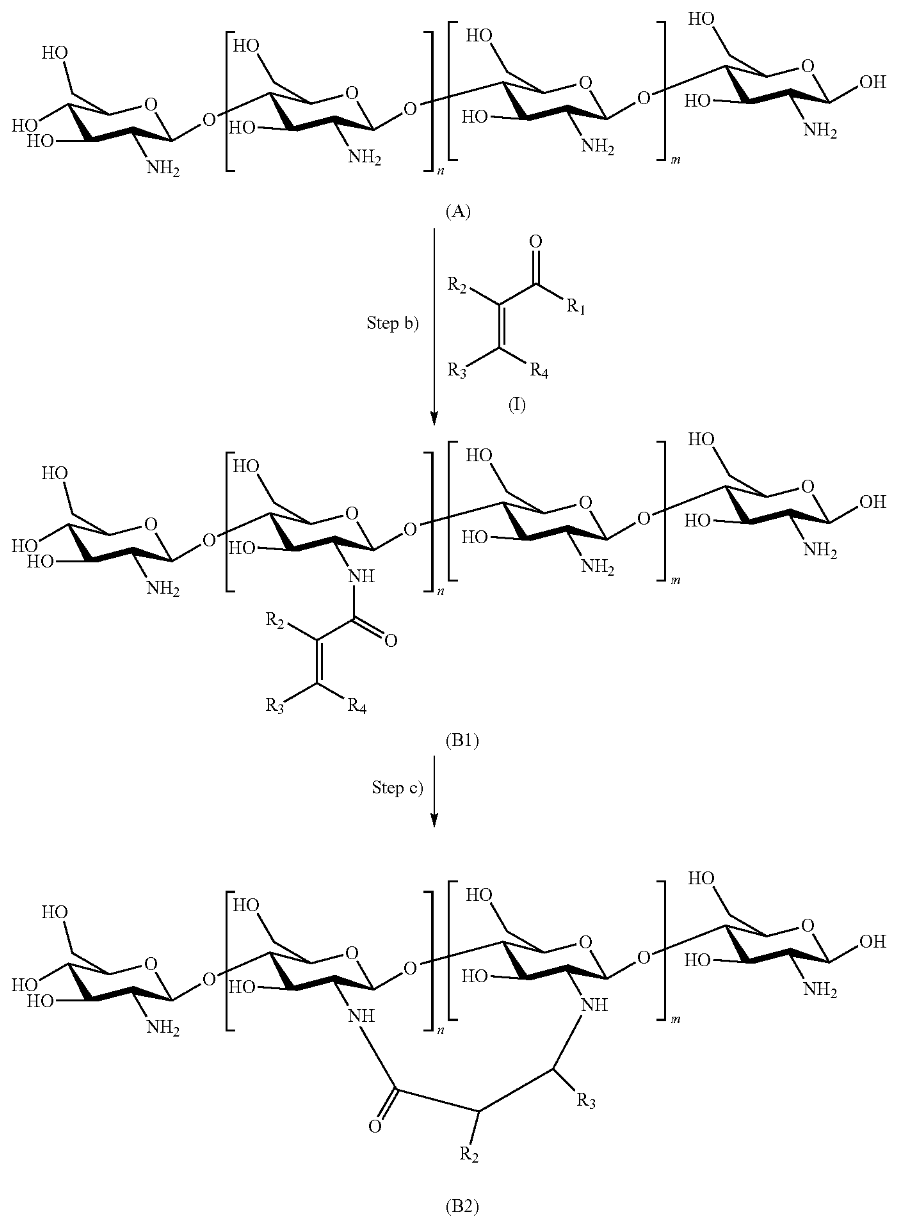

(A)

(I)

(B1)

(B2)

wherein a chitosan (A) wherein m is a integer comprised between 1 and 12'500 and n is a integer comprised between 1 and 12'500, is first provided in a swollen state in an aprotic solvent at room temperature and then the amino groups of said chitosan are acylated with an acrylic compound (I) and the resulting acylation product (B1) is then reacted in presence of a base to lead to a cross-linked chitosan (B2) which can then be isolated by purification to lead to a purified cross-linked chitosan according to the invention.

According to a particular embodiment, the chitosan can be provided in swollen state, even in dissolved state, in a protic solvent but in this case, side reactions of hydrolysis of the acylating agent can occur and this must be taken into account when calculating reaction loads. Additionally, in this case, it will be necessary to wash the acylated chitosan obtained under step b) to remove the hydrolysis products of the acylating agent before the stage of aza-Michael reaction under step c).

According to a particular embodiment, the chitosan is provided in absence of water and the acylating step is carried out in absence of water. The absence of water advantageously leads to higher yields and avoid the formation of side products.

According to a particularly advantageous aspect, the acylation step is conducted in absence of water. In this case, an aprotic solvent can be used as reaction medium or a supercritical fluid. According to a particular embodiment, the aprotic solvent is a polar aprotic solvent such as for example selected from DMF and DMSO. In a particular embodiment, a supercritical fluid can be a supercritical solvent such as carbon dioxide, nitric oxide (I), freons (chloro(bromo)(fluoro)hydrocarbons) which is used to provide the acylating agent to the reaction medium and then acylation reaction carried out after removal of the supercritical solvent from the reaction medium, for example by lowering the pressure below the critical value.

According to a further particularly advantageous aspect, the acylation step is conducted an anhydrous aprotic medium.

According to a particular aspect, a polar aprotic solvent is selected from dimethylformamide (DMF), dimethylacetamide, acetonitrile (MeCN), N-methylpyrrolidone, dimethyl sulfoxide (DMSO) or a mixture thereof.

According to another particular aspect, dichloromethane, dichloroethane, chloroform, and other chloro(fluoro)hydrocarbons can be also used as a polar aprotic solvent, but when conducting the aza-Michael reaction step c), those solvents should be distilled off right before the provision of the base. It is desirable to perform such distillation at temperatures not exceeding 60° C., which is feasible at atmospheric pressure for most of the mentioned solvents. If a high-boiling solvent was used, distillation must be carried out under reduced pressure.

According to another particular aspect, ethers and esters, ketones can also be used as solvents for the reaction steps a) to c) under anhydrous conditions but reactions in such solvents will proceed more slowly. For example, diethyl ether, diisopropyl ether, methyl tert-butyl ether, methyl acetate, ethyl acetate, propyl acetate, butyl acetate, acetone, methyl ethyl ketone and diethyl ketone can be used.

According to a particular aspect of the invention, the acylation step b) can be conducted by any method described in the context of acylation of glucosamine with acryloyl chloride (Zhang et al., 2017, *Biomacromolecules,* 1, 3, 778-786; Bu et al., 2017, *Advances,* 7, 76, 48166-48175) or methods described as useful for the acylation of an amino group such as methods using i) a carbodiimide; ii) an azide; iii) mixed anhydrides; iv) an activated ester and v) others methods described below.

Known acylation methods using carbodiimide with the formation of intermediate enol esters can be used under step b) (WO 2019/60740; Hao-Bin et al., 2018, *Carbohydrate Polymers,* 196, 359-367). If N,N'-dicyclohexylcarbodiimide (DCC) can be used as condensing agent, 1-ethyl-(3-(3-dimethylamino)propyl)-carbodiimide hydrochloride and N-cyclohexyl-N'-(2-morpholinoethyl)carbodiimide methyl p-toluenesulfonate (CAS Registry Number: 2491-17-0) would be preferred.

Known acylation methods using azides can be used under step b) (Honzl et al., 1961, *Coll. Czech. Chem. Commun.,* 26, N. 9, 2333-2344).

Known acylation methods using mixed anhydrides can be used under step b) (Wieland et al., 1951, *Ann. Chem.,* 572, N3, 190-194; Belleau et al., 1968, *J. Amer. Chem. Soc.,* 90, N 6, 1651-1652; Gorecka et al., 1978, *Synthesis*, N 6, 474-476; Diago-Meseguer et al., 1980, *Synthesis, N* 7, 547-551; Leplawy et al., 1960, *Tetrahedron,* 11, N 1, 39-51). The use of internal anhydrides is also possible for acylation, for example maleic anhydride (Liwschitz et al. 1957, *Journal of the Chemical Society,* 4399; Kang, et al., 2014, *Bioorganic and Medicinal Chemistry Letters,* 2, 10, 2364-2367; US 2016/200730; Sanchez et al., 2010, *Anna European Journal of Organic Chemistry,* 13, 2600-2606). Known acylation methods using activated esters through the formation of activated amides can be used under step b) such as a carbonyldiimidazole method (Paul et al., 1960, *J. Amer. Chem. Soc.,* 82, N 17., 4596-4600), a cyanomethyl ester method (Schwyzer et al., 1955, *Helv. Chim. Acta,* 38, N 1, 80-83), a thiophenyl ester method (Wieland et al., 1951, supra), a substituted phenyl ester method (Gross et al., 1983, Mayenhofer, editors. Moscow: Mir., P. 421), an ester method with heteroaromatic compounds together with carbodiimide method (Jakubke et al., 1966, *A. Chem. Ber.,* 99, N8, 2419-2429; Taschner et al., 1965, *Ann. Chem.,* 690, 177-181), a method of esters with hydroxylamine derivatives together with carbodiimide method (Losse et al., 1964, *Ann. Chem.,* 678, 185-190; Nefkens et al., 1961, *Amer. Chem. Soc.,* 83, N 5, 1263; Anderson et al., 1963, Ibid, 85, N 19, 3039; Konig et al., 1970, *Chem. Ber.,* 103, N 3, 788-798), interesterification methods (variant of the ester method) (Sakakibara, 1965, *Bull. Chem. Soc. Jap.,* 38, N 1, 1979-1984; Fujino et al., 1968, *Ch. Chem. Pharm. Bull.,* 16, N 5, 929-932; Gudkov et al., 1978, 48, 9, 2146; Devadas et al., 1979, *Ind. J. Chem., B*16, N 11, 1026-1027).

Other known acylation methods can be used under step b) such as ketenimine method (Stevens et al., 1958, *J. Amer. Soc.,* 80, N 15, 4069-4071); Acetylene derivatives method (Arens, 1955, *Rec. Trav. Chim.,* 74, N 6, 759-770; Gais 1978, Aktivierungsmittel für Peptidsynthesen *J. Angew. Chem. Int. Ed,* 90 (8), 625-626 doi.org/10.1002/ange.19780900808); method using derivatives of cyanamide (Losse et al., 1960, *Ann. Chem.,* 636, 144-149); Synthesis using iIsoxazolium salts (Woodwart et al., 1961, *J. Amer. Chem. Soc.,* 83, N 4, 1010-1012); Synthesis using imidoyl halides (Bergmann et al., 1936, *J. Biol. Chem.,* 115, N 3, 93-611).

According to a particular embodiment, the acrylic compound of Formula (I) can be an acid, an acid halide, an active ester (e.g. 3-hydroxybenzotriazole ester, N-hydroxysuccinimide, pentachlorophenol, 2-nitro-4-sulfophenol esters and esters having other similar leaving groups), an anhydride or mixtures thereof.

According to a particular embodiment, the acrylic compound of Formula (I) is selected from the following group:

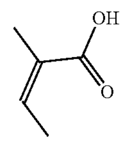

(angelic acid, CAS Registry Number: 565-63-9);

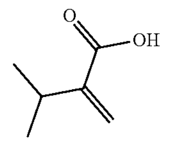

(2-iso-propyl acrylic acid CAS Registry Number: 4465-04-7);
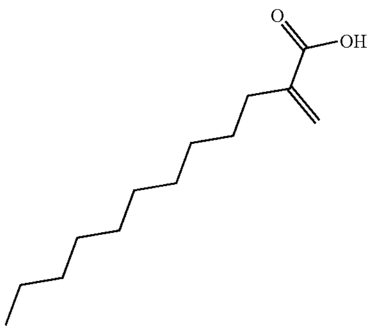
(2-methylenedodecanoic acid, CAS Registry Number: 52756-21-5);
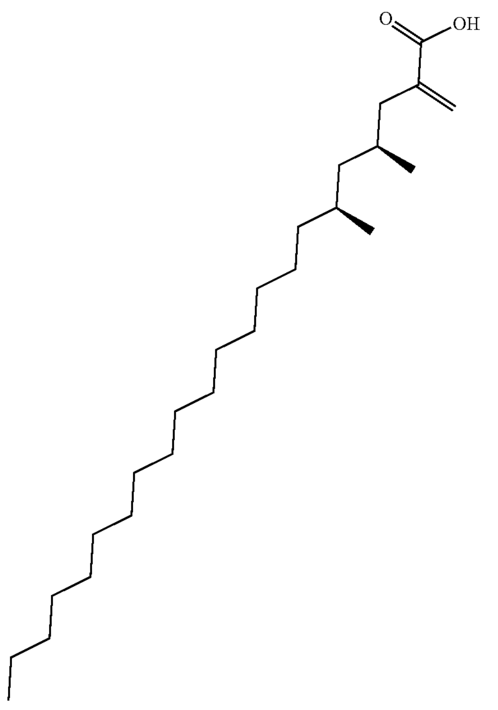 [SMILES: C=C(C[C@@H](C)C[C@@H](C)CCCCCCCCCCCCCCCC)C(=O)O]
(4S,6S)-4,6-dimethyl-2-methylenedocosanoic acid;
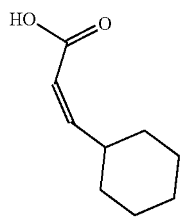 [SMILES: O=C(O)/C=C\C1CCCCC1]
((Z)-3-cyclohexylpropenoic acid, CAS Registry Number: 673456-32-1);
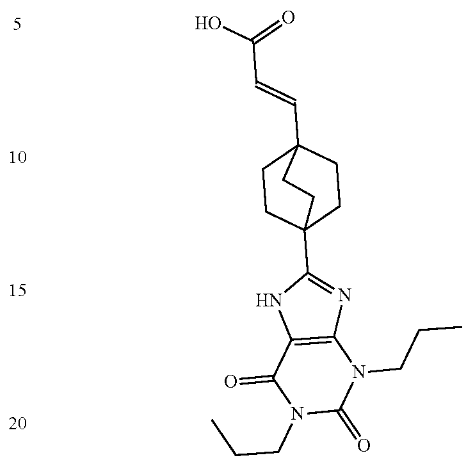
((E)-3-[4-(2,6-dioxo-1,3-dipropyl-2,3,6,7-tetrahydro-1H-purin-8-yl)-bicyclo[2.2.2]oct-1-yl]-acrylic acid, CAS Registry Number: 340021-16-1);
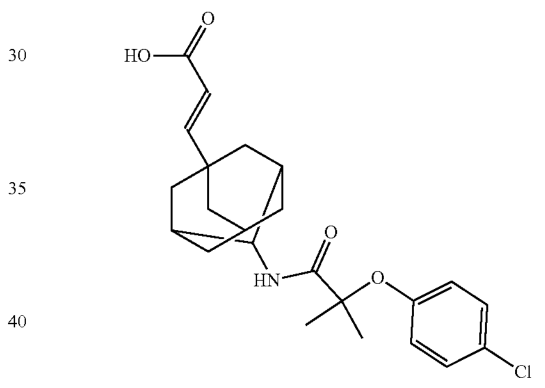
((2E)-3-((E)-4-{[2-(4-Chlorophenoxy) methylpropanoyl]amino}-1-adamantyl)acrylic acid;
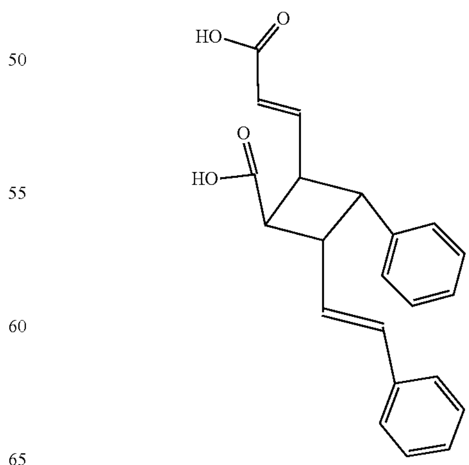

(3-(2-carboxy-4-phenyl-3-styryl-cyclobutyl)-acrylic acid, CAS Registry Number: 34271-87-9);

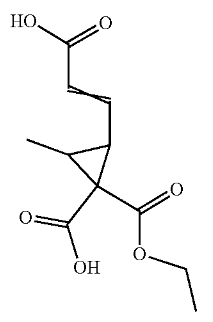 [SMILES: CCOC(=O)C1(C(=O)O)C(C)C1C=CC(=O)O]

(3-Methyl-2-acrylsaeure-(1)-cyclopropan-carbonsaeure-(1)-carbonsaeure-(1)-aethylester, CAS Registry Number: 91971-88-9);

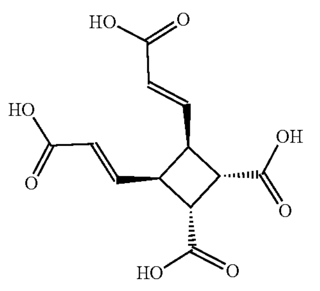 [SMILES: O=C(O)/C=C/[C@@H]1[C@H](/C=C/C(=O)O)[C@@H](C(=O)O)[C@H]1C(=O)O]

(3t,4t-Dicarboxy-cyclobutan-1,2c-di-(trans-acrylic acid), CAS Registry Number: 55011-62-6);

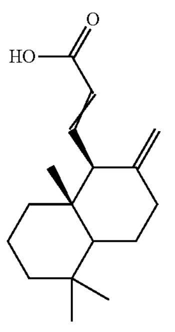 [SMILES: C=C1CCC2C(C)(C)CCC[C@]2(C)[C@H]1C=CC(=O)O]

coronadiene;

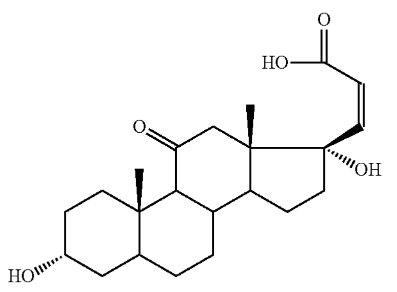 [SMILES: C[C@]12CC[C@@H](O)CC1CCC1C2C(=O)C[C@@]2(C)C1CC[C@]2(O)/C=C\C(=O)O]

(CAS Registry Number: 1247-53-6)

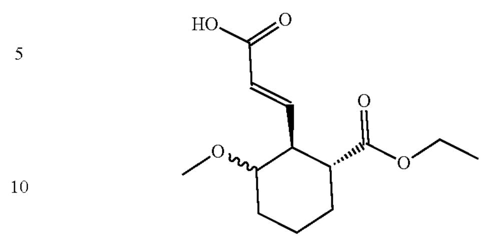

((E)-3-(2t-Ethoxycarbonyl-6ξ-ethoxy-cyclohexan-1r-yl)-acrylic acid, CAS Registry Number: 2960-11-4); cinnamic acid; 4-methylcinnamic acid; p-nitrocinnamic acid; caffeic acid;

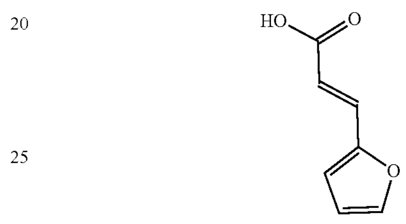

(3-(fur-2-yl)crotonic acid; 3-(2-furyl)acrylic acid, CAS Registry Number: 539-47-9);

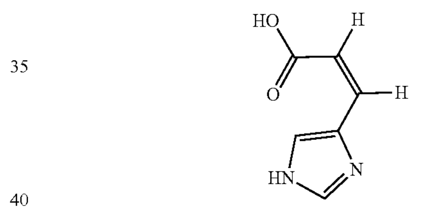

((Z)-urocanic acid CAS Registry, Number: 7699-35-6);

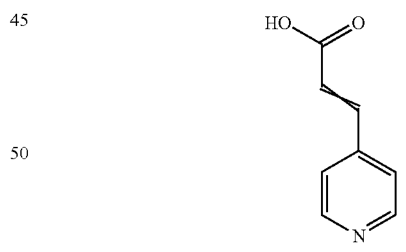

(3-(4-pyridinyl)-2-propenoic acid; 3-(pyridine-4-yl)acrylic acid, CAS Registry Number: 5337-79-1) argutinosides A-I;

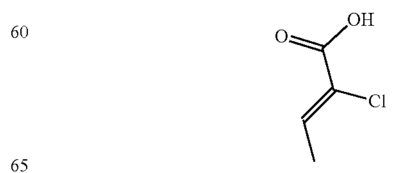

((Z)-2-Chloro-but-2-enoic acid, CAS Registry Number: 53993-41-2);
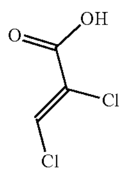
((2Z)-2,3-dichloroprop-2-enoic acid, CAS Registry Number: 3533-68-4),
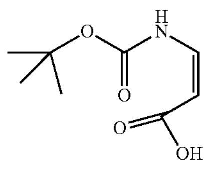
cis N-tert-butyloxycarbonyl dehydro β-alanine, CAS Registry Number: 151292-68-1),
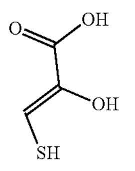
(2-hydroxy-3-mercapto-acrylic acid, CAS Registry Number: 6228-60-0;
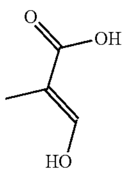
hydroxy(meth)acrylic acid;
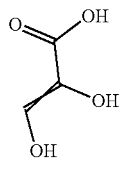
(dihydroxy-acrylic acid, CAS Registry Number: 2702-94-5);
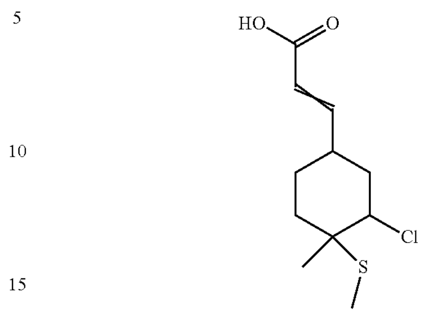
(Reaxys ID 2721331);
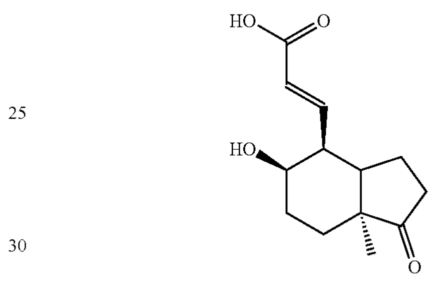
(CAS Registry Number: 64361-31-5);
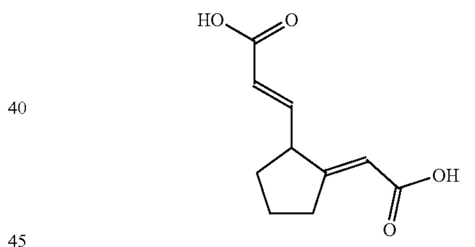
3-(2-carboxymethylene-cyclopentyl)-acrylic acid;
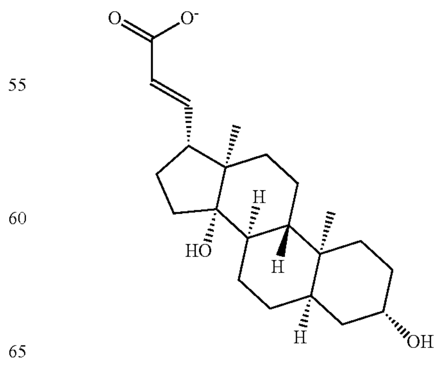

(CAS Registry Number: 78727-62-5):

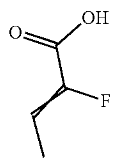

(fluoro butenoic acid, CAS Registry Number: 2365-87-9);

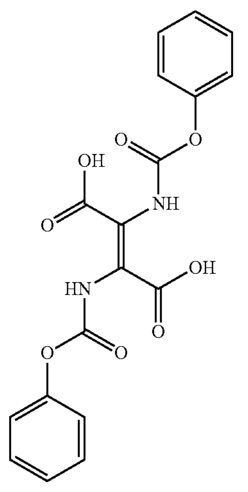 [SMILES: O=C(N/C(C(=O)O)=C(/NC(=O)Oc1ccccc1)C(=O)O)Oc1ccccc1]

((E)-2,3-bis(phenoxycarbonylamino)but-2-enedioic acid);

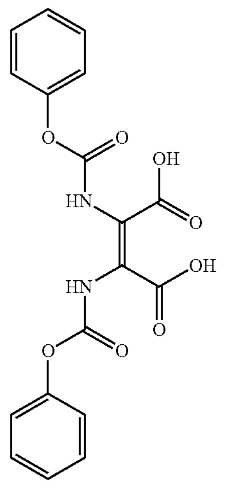 [SMILES: O=C(N/C(C(=O)O)=C(\NC(=O)Oc1ccccc1)C(=O)O)Oc1ccccc1]

((Z)-2,3-bis(phenoxycarbonylamino)but-2-enedioic acid);

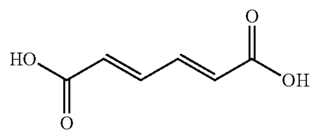

(2E,4E)-2,4-hexadienedioic acid (muconic acid), maleic acid; fumaric acid;

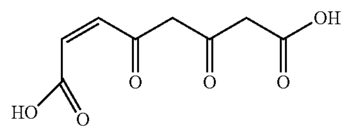 [SMILES: O=C(O)/C=C\C(=O)CC(=O)CC(=O)O]

(maleylacetoacetic acid, CAS Registry Number: 5698-52-2); (E)-4-(methylamino)-4-oxobut-2-enoic acid, acrylic derivative of glutamic acid

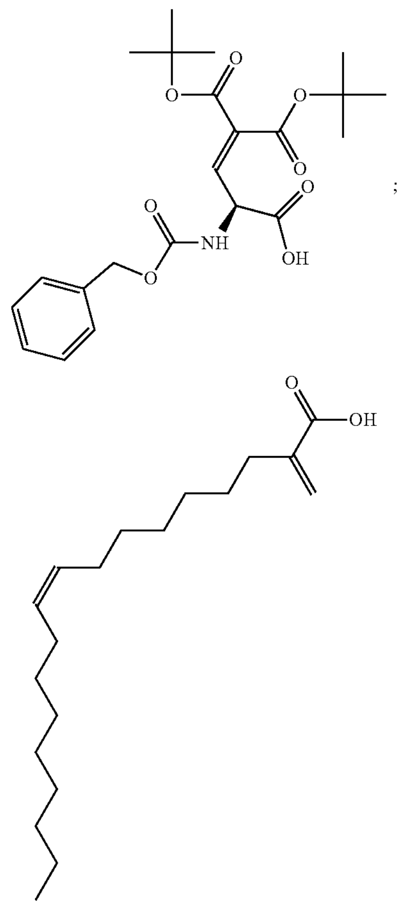

;

(2-methylene-9(Z)-octadecenoic acid, CAS Registry Number: 33780-98-2);

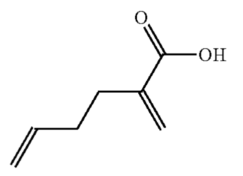

(2-methylene-5-hexenoic acid (2-methylenehex-5-enoic acid), CAS Registry Number: 73505-05-2);

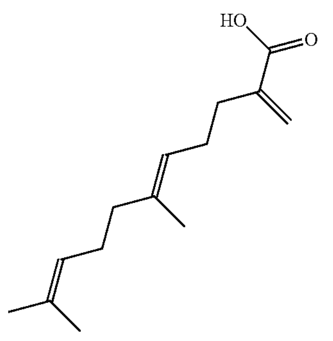 [SMILES: C=C(CC/C=C(\C)CCC=C(C)C)C(=O)O]

((E)-6,9-dimethyl-2-methylideneundeca-5,9-dienoic acid, CAS Registry Number: 1580541-76-9);

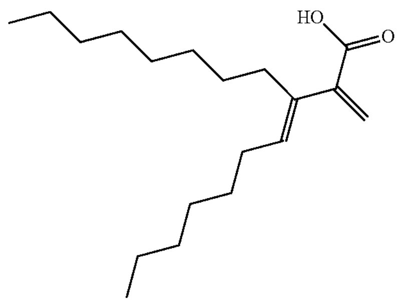 [SMILES: C=C(C(=O)O)/C(=C/CCCCCC)CCCCCCCC]

(2-(cis-7,8-hexadecenyl)-acrylic acid);

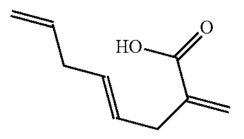

((E)-2-methyleneocta-4,7-dienoic acid);

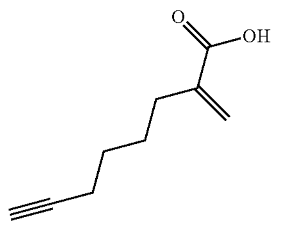

(2-methylene-7-octynoic acid, CAS Registry Number: 127559-93-7); and

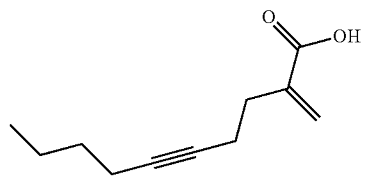

(2-methylene-5-decynoic acid, CAS Registry Number: 150254-20-9); and an acyl halide ($R_1$=Halogen), in particular acryloyl chloride;

( 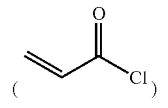 )

or methacryloyl chloride.

According to a further particular embodiment, the acrylic compound is an acyl halide ($R_1$=Halogen), in particular acryloyl chloride ( 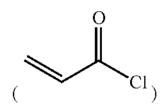 )

or methacryloyl chloride.

According to a particular aspect, when the acrylic compound used under the acylation step b) is an acid halide, it is important to avoid the presence of water in the reaction system, since an undesirable side process of hydrolysis of the acid halide will occur, leading to acrylic acid and this can lead to the functionalization of the nanoparticles by carboxyl groups during the Michael addition reaction of the free acrylic acid to the amino groups of chitosan.

According to a particular aspect, the acrylic compound used under the acylation step b) is an acid chloride (e.g. acyl chloride). According to one aspect, the use of an acid chloride advantageously results in the formation of hydrogen chloride that does not interfere with the next reaction step in the presence of excess of base and is easily removed in the form of salts during dialysis.

It is important to note that the acylation of amines with carboxylic acid halides leads to the production of one equivalent acid, which will form a salt with unreacted amine and diminish the yield of a method of the invention. Therefore, when acid halide is used under the acylation step b), the addition of an equivalent amount of a base, preferably a non-nucleophilic base (e.g. triethylamine is used under step b) to neutralise this acid.

According to a particular aspect, when the acrylic compound used under the acylation step b) is an acid anhydride, the method of the invention further comprises a step of washing the reaction medium and removing the formed acid to avoid the presence of water in the reaction system before conducting step c). In particular, the formed acid can be washed off from the acylation product with a solvent through a filter, or by dialysis against a solvent or by suspending the acylation product in a solvent and centrifuging with discarding the supernatant.

According to another particular aspect, when using condensing agents (e.g. DCC) for acylation with free acid, it is necessary to carefully control the completeness of the reaction and it is preferable to nevertheless include a washing step as a precaution. For example, when a condensing agent such as DCC is used as condensing agent, by-products are formed, such as dicyclohexylurea, during the acylation reaction which needs to be removed from the reaction mass before conducting the next step so that it is not involved in the formed cross-linking leading to the nanoparticles of the invention.

According to another particular embodiment, under step c) the base is used in a molar excess sufficient to form an alkaline medium which neutralizes the hydrogen halide formed under step b). Typically, the molar excess of the base is at least a 10% molar excess (e.g. about 20 to 40% molar excess) which would correspond to at least 1-3 molar excess in relation to the amino groups of the resulting acylation product of step b).

According to another particular embodiment, the cross-linked chitosan obtained under step c) can be purified under step d) by standard techniques to remove salt impurities and/or the remaining aprotic solvent such as by dialysis or washing steps with a solvent such as water or methylene chloride, methanol, ethanol, acetone and the like, followed by centrifugation or using supercritical solvents such as use carbon dioxide in which the formed nanoparticles of the cross-linked chitosan are insoluble or by removing the aprotic solvent by evaporation and then washing out the by-products from the cross-linked chitosan product with a solvent through a filter, for example a filter having pores not more than 40 μm. According to a more particular embodiment, hydrophobic filter elements of fine porosity, such as polypropylene or PTFE can be advantageously used, since their hydrophobicity creates additional obstacles for the penetration of hydrophilic chitosan nanoparticles through them.

According to another particular embodiment, the purified cross-linked chitosan obtained under step d) can be dried, e.g. under an optional further drying step e).

According to a particular aspect, the base used under step c) for the Michael addition reaction is an essentially pure non-nucleophilic base, in particular essentially free from the presence of secondary amines.

According to a particular aspect, the Michael addition step c) is conducted in a protic solvent such as water. In this case, it is necessary to control the degree of saponification, for example by measuring both the amount of carboxyl groups formed and the formed amino groups at the acylation stage. Accurate method for carboxyl groups, since their concentration is usually one to two orders of magnitude lower, and the difference in the number of amino groups can be within the experimental error would be NMR, IR spectroscopy, or acid-base titrations, such as described in Glazunov et al., 1999, 25(3), 216-219; Brugnerotto et al., 2001, *Polymer,* 42, 3569-3580 or Kubota, et al., 2000, *Carbohydrate Research,* 324, 268-274. However, a protic solvent at this step might be advantageous when the obtaining of saponified cross-linked chitosan nanoparticles are wished at the end of step c) or if it is planned to repeat the acylation step as described below in order to saturate the nanoparticles with carboxy functions and then achieve cross-linking in excess. In fact, when the nanoparticles are saturated with carboxy functions, the saponification step is carried out. Next, the steps of acylation and aza-Michael are repeated, followed by saponification. If spontaneous saponification occurs during the aza-Michael step in a protic solvent this is not disadvantageous since saponification is anyway carried out afterwards and the fact that it partially occurs during the aza-Michael reaction would not be a problem.

According to another particular aspect, the Michael addition step c) is conducted in absence of water which can be achieved by the use of an aprotic solvent as reaction medium or by using a base as a solvent.

According to another particular embodiment, the Michael addition reaction step is carried out in alkali medium such that for each amide bond formed during the acylation step, one equivalent of secondary amine is formed after the Michael addition reaction, thereby leading that even in case of a cross-linking of all amino groups, at least half of the amino groups remain available for salt formation. This can be checked by acid-base titration, IR and NMR spectrometry such as described in Glazunov et al., 1999, 25(3), 216-219; Brugnerotto et al., 2001*, Polymer,* 42, 3569-3580 or Kubota, et al., 2000*, Carbohydrate Research,* 324, 268-274. According to a particular aspect, the intramolecular addition reaction inside the chitosan macromolecule is significantly preferable to the intermolecular reactions, due to statistical and steric factors, thereby leading to a high yield in cross-linking.

The resulting nanoparticles after Michael's addition reaction step c) can be subjected to a reduction (e.g. by reacting with complex metal hydrides, diboran, cyanoborohydride and others derivatives of borohydride) in order to transform the amide groups into a secondary amines and increase the possible degree of ionization of the nanoparticles. The possible degree of ionization of the nanoparticles depends on the number of amino groups. The more amino groups present, the greater the opportunity for the formation of salts and, respectively, ionization to occur. The degree of ionization can be assessed by acid-base titration, IR and NMR spectrometry.

According to a further aspect, the cross-linked chitosan product obtained under step c) or step d) or the corresponding dried product obtained step e) can be subjected to a saponification step f) under alkaline conditions (e.g. in presence of an aqueous base in excess) in a protic solvent in order to increase the solubility of the cross-linked chitosan nanoparticles on a wider pH range, e.g. under physiological weakly alkaline conditions (e.g. about pH is 7.2-7.3). If the solvent used under steps c) or d) does not allow saponification (e.g. like DMF), saponification needs to be carried out after purification step d) in a solvent allowing saponification or by re-suspension of the dried cross-linked chitosan in a solvent allowing saponification after step e) such as in ethers as solvents. For example, under this further step f) an aqueous base is added to the product obtained under steps c) or d) in a molar excess compared to the amount of the acylating agent used under step b), such as for example about 10 times or 100 times the molar amount of such acylating agents. As schematized under Scheme 2 below, the amide groups of the cross-linked chitosan (B2) are hydrolyzed into corresponding carboxyl groups in a product (B3) available for the formation of the corresponding salts.

Scheme 2

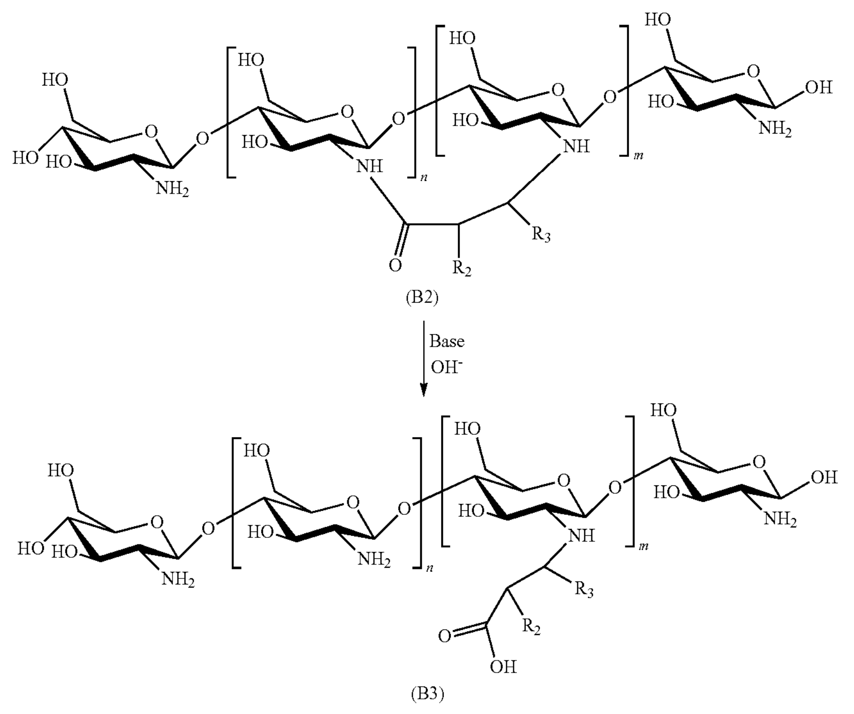

(B2)

(B3)

This allows regenerating half of the amino groups in the cross-linked chitosan as primary amine, the second half becoming secondary amines, which are now alkylated with propionic acid (or substituted propionic acid). For example, saponification of a cross-linked chitosan can be conducted by the addition of 1 molar aqueous solution of sodium hydroxide at 50 degrees Celsius for an hour. The obtained product (B3) can then be subjected again to an acylation step b) as schematized in Scheme 3a and Scheme 3b below wherein in this case the acylation occurs under the same conditions wherein acylation of both primary (Scheme 3a) and secondary (de novo acylation of amino groups obtained at stages b, c, or f, Scheme 3b) amino groups are possible can occur. The obtained product (B4) is then subjected again to a Michael's addition reaction under step c) to achieve a cross-linking of all amino groups and obtain an essentially fully cross-linked chitosan (B5).

Scheme 3a

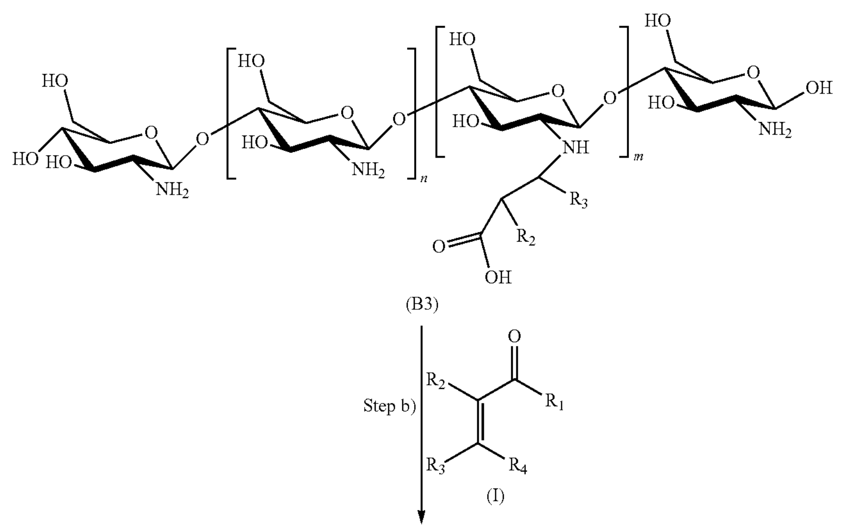

(B3)

(I)

-continued
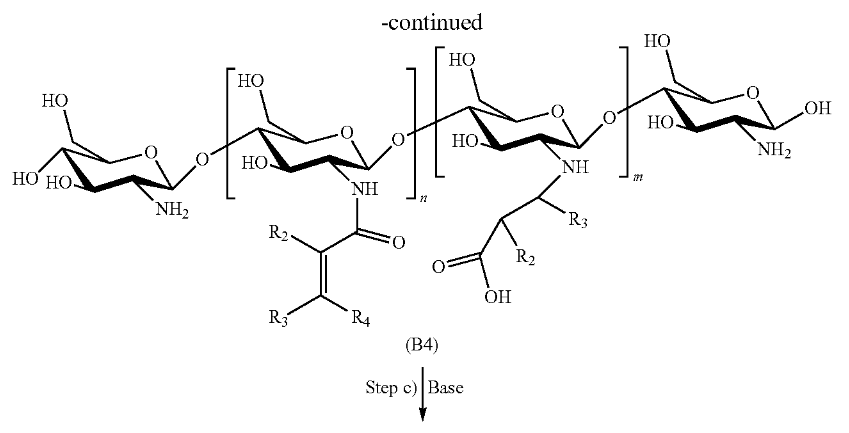
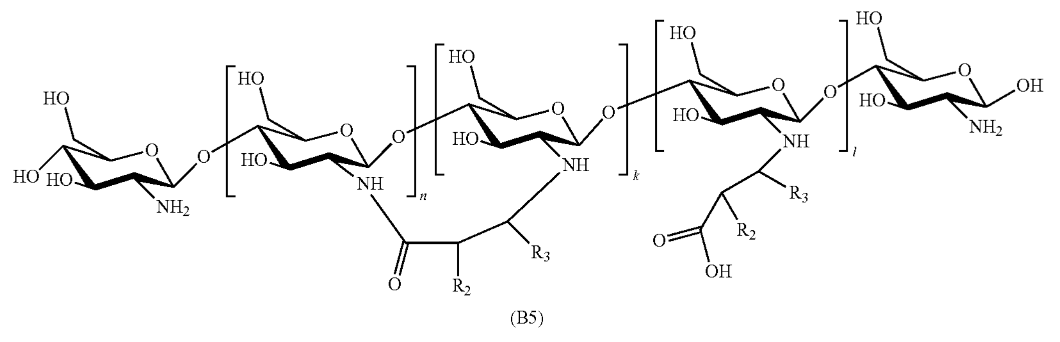
Scheme 3b
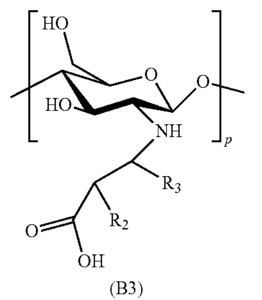
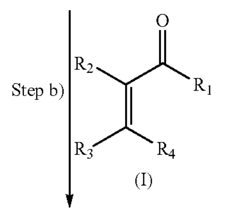
-continued
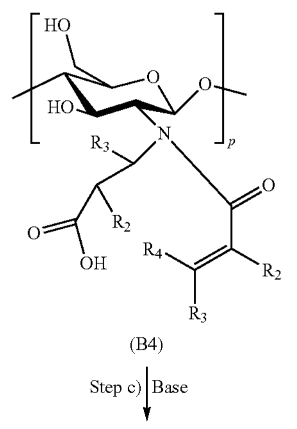

-continued

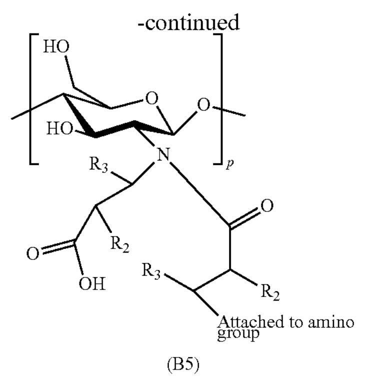

(B5)

In this case, in the obtained product, internal salts are formed with the carboxyl groups, which will be half of the initial content of amino groups present at the end of the first synthesis step c). According to a particular aspect, such a product will contain essentially the same number of carboxyl groups, total secondary and tertiary amino groups, amide functions (excluding the initial acetylaminoglycoside fragments), i.e. That is, such a product will comprise a complete internal salt, all carboxyl groups being balanced by amino groups.

While without wanting being bound by any theory, it can be considered that if amino groups are present in the initial chitosan provided under step a), then, providing their exhaustive derivation is achieved under step b), X amino groups are acylated with the acylating agent and therefore, X amino groups will be subjected to aza-Michael reaction with acyl fragments grafted to chitosan under step c). After saponification of the amide groups formed in step b) present in the product of step c) subjected to the saponification step f), X primary amino groups are regenerated, X carboxyl groups are available from the acrylic acid used in the acylation, and X secondary amino groups resulting from step c) still remain. Thus, with repeated exhaustive derivation by acylation, X regenerated primary amino groups can be further acylated (the secondary amino groups that we obtained in step c) can probably be acylated, but this is a less likely process). Then, when repeating step c), the secondary amino groups obtained earlier in step c) enter the aza-Michael reaction to form X tertiary amino groups.

Further, conducting a saponification for the second time again regenerates X primary amino groups and X tertiary amino groups remain which are not subject to saponification and X carboxyl groups are formed. Thus, the total number of carboxyl groups will be 2X, primary amino groups X, tertiary amino groups X and the polymer will become electrically neutral and form internal salts.

If exhaustive derivation is carried out for a third time, then, only X/2 acylating agent is needed, since only X amino groups remain capable of entering into these reactions and all these amino groups are primary. Thus, after the third derivation sequence (steps b) to c)) and saponification (step f), only 2.5X carboxyl groups, 1.5X tertiary amino groups, 0.5X primary amino groups are obtained and the polymer will become anionic with a 0.5X excess of carboxyl groups. Therefore, repeating this reaction sequence shall each time give an increase in the number of carboxyl groups in increments of 0.25, 0.125, 0.0625, 0.03175 etc. The present of carboxyl groups can easily be confirmed by infrared or by acid-base titration, and also by the mass spectrometry.

According to a particular embodiment, the amount of alkali used under optional saponification step f) is in equimolar amounts with the amide groups obtained in the first reaction step c)/d) or e) to be saponified and up to 10 times molar excess.

According to a particular embodiment, at least one sequence of steps b) to c) (or d)/e)) is carried out with a saponification step f) as the end of the Michael addition before re-subjecting to new sequence of acylation steps b) to c) (or d)/e)).

According to a further particular embodiment, about 2 to 6 reaction sequence of steps a) to f) is carried out.

According to another particular embodiment, the reaction sequence of steps a) to f) is repeated once or twice.

According to a particular embodiment, after each sequence of steps a) to f), solubility of the cross-linked chitosan is obtained in a wider range of pH and the properties of native chitosan may be modified, for example in terms of mucotropy and penetration into cells. Therefore, those properties can be advantageously adjusted, depending on the number of reaction sequence performed and the obtained cross-linked chitosan nanoparticles can be useful for the delivery of compounds of interest.

According to a particular embodiment, cationic (e.g. cationic peptides such as sequences enriched in arginine, ornithine or lysine or neutral substances in terms of electric charge can be delivered by a cross-linked chitosan according to the invention.

According to another particular embodiment, cross-linked chitosan according to the invention can be used to formulate those compounds for protecting them from degradation (e.g. by proteolysis) or from the binding of non-desirable substances (e.g. antibodies or other macromolecules) or for ensuring a slow release of the soluble for of those compounds.

According to another particular embodiment, biologically active material can be integrated within the formed nanoparticles, either after the first acylation step b) or the first Michael addition step c). According to a further particular embodiment, a biologically active material can be either covalently attached, or adsorbed or fixed in the form of salts or encapsulated within the cross-linked chitosan nanoparticles of the invention.

In the case where a saponification step is carried out, covalent cross-linking of a biologically active agent would be destroyed but ionic bonds with the biologically active agent can be formed within the salts of the formed cross-linked chitosan.

Alternatively, the nanoparticles can be impregnated with biologically active substances resistant to reagents used in steps a) to f) when a sequence of these steps is applied such as clusters of heavy elements to create radiopaque nanoparticles.

Further alternatively, multifunctional, labile, biologically active substances are preferably introduced by diffusion into cross-linked chitosan nanoparticles of the invention after their synthesis, or using click chemistry, methods of immobilization of enzymes, proteins, nucleic acids and antibodies.

According to a particular aspect, integration of a biologically active material within the chitosan nanoparticles of the invention can be achieved by impregnation of the product resulting from step b) or c) with the desired biologically active material. For example, a solution of a biologically active material in an aprotic solvent can be added to the product resulting from step b) before conducting the Michael addition step c). Alternatively, the acetylated chitosan product resulting from step b) can be dissolved in a solvent suitable to the further synthesis conditions.

Impregnation can be performed without dissolving the cross-linked chitosan of the invention.

In view of impregnation of the cross-linked chitosan of the invention with a biologically active agent, the biologically active agent/substance can be dissolved in a polar aprotic solvent or in any other. If a protic solvent is used, then, before the aza-Michael reaction, it is desirable to remove it and dry the impregnated product. For impregnation, supercritical fluids can be used as described in Weidner 2018, *The Journal of Supercritical Fluids,* 134, 220-227 doi.org/10.1016/j.supflu.2017.12.024; Duarte et al., 2007, *The Journal of Supercritical Fluids,* 42 (3), 373-377 doi.org/10.1016/j.supflu.2007.01.007 which provides extremely high degree and high-quality impregnation. It is also possible to use electrophoresis methods as described in Boccaccini et al., 2010, *J. R. Soc. Interface,* 7, S581-S613 doi.org/10.1098/rsif.2010.0156.focus; Pishbin et al., 2013, *Acta Biomaterialia,* 9 (7), 7469-7479 or "gene gun" method as described in Zhao et al., 2012, *PLOS One,* 7 (10): e46765. doi: 10.1371/journal.pone.0046765, if the impregnating of the agent can be accelerated by the methods of Coulomb. For example, an aqueous solution of a biologically active material such as an antibiotic can be mixed with an aqueous solution of chitosan acylated after step b) and subjected to evaporation with azeotropic distillation of water, spray drying, lyophilization, and other drying methods to obtain the acylated chitosan impregnated with the biologically active material in dry state. Then, the dried material is subjected to an excess of a non-nucleophilic base to deionize the amino groups of chitosan and the resulting mixture is then subjected to the Michael addition reaction step c).

According to a further aspect, the chitosan provided under step a) has a mean molecular weight ranging from about 5 to about 2'000 kDaltons, in particular from about 150 to 2'000 kDaltons.

According to another further aspect, the chitosan provided under step a) has a degree of deacetylation from about 100% (as in glucosamine) to about two deacetylated fragments per macromolecule, which, for example, for chitosan (chitin) with molecular mass 300 kDa is about 0.14%.

Suitable chitosan that can be used as starting material in method of the invention can be of various origins, including natural (animal or fungal), in particular from shells of crab and shrimp, exoskeleton of insects, higher fungi, cultures of unicellular mushrooms. Chemically or enzymatically synthesized chitosan may also be used.

According to a further aspect, the chitosan provided under step a) is left to swell for about 5 minutes to about 1 day, preferably in an aprotic solvent.

According to another further aspect, the deacetylation step b) is carried out at a temperature of from about −70° C. (beginning of the reaction) to about +150° C. (completion of the reaction), preferably from about +2° C. (beginning of the reaction) to about +55° C. (completion of the reaction). The reaction time is from about 0.5 hour to 10 days, preferably about 2.5 hours at about +20 to about +30° C., preferably under ultrasonic action as mixing means.

According to another further aspect, the Michael addition step c) is carried out at a temperature of from about −70° C. (beginning of the reaction) to about +150° C. (completion of the reaction), preferably from about +20° C. (beginning of the reaction) to +55° C. (completion of the reaction). The reaction time is from about 0.5 hour to 10 days, preferably about 15-18 hours at about +20° C. and about 6 hours at about +55° C., preferably under ultrasonic action as mixing means.

According to another further aspect, the drying step of the cross-linked chitosan is conducted by freeze drying under step e).

According to another further aspect, the optional additional saponification step f) is carried out at a temperature from about 0° C. (beginning of the reaction) to about +140° C. (completion of the reaction), preferably from about +20° C. (beginning of the reaction) to about +55° C. (completion of the reaction). The reaction time is from about 0.5 hour to 10 days, preferably about 2-6 hours at +55° C., preferably with ultrasonic action as mixing means.

In particular embodiment, nanoparticles of the invention are spontaneously formed by the material obtained under steps b) and c) of a method of the invention. Those particles are very stable over time. For example, a 2% solution at room temperature is stable for at least a year and for at least several years in dry state.

According to an aspect of the invention is provided a method for the preparation of a drug delivery system for a bioactive agent comprising the step of conducting a method of the invention wherein a bioactive agent is added under step b), c), d) or e).

According to an aspect of the invention is provided a method for the preparation of a drug delivery system for a bioactive agent comprising the step of:

- Providing a cross-linked chitosan of the invention in wet or dry state;
- Providing a bioactive agent to be delivered;
- Dissolving the bioactive agent in a solvent or a supercritical fluid;
- Loading the nanoparticles of the said cross-linked chitosan of the invention by either impregnating the cross-linked chitosan with the solution of a bioactive agent or by direct introduction into nanoparticles by electrophoresis or acceleration by an electric field;
- Collecting the so-obtained composition or nanoparticles loaded with bioactive agent (e.g. drug).

According to another particular embodiment, is provided a method for identifying a cross-linked chitosan obtainable from a method according to the invention, said method comprising the steps of:

- providing a chitosan to be characterized in a solvent (e.g. methylene chloride or chloroform);
- acylating said chitosan as described herein (e.g. as acetyl chloride or acetic anhydride) under vigorous stirring such as for about 0° C. to about 20° C., such as about 30 minutes;
- neutralizing the reaction medium with a base (e.g. diisopropylethylamine as non-nucleophilic base);
- evaporating the solvents and washing the obtained neutralized product;
- subjecting the product to a reflux acid hydrolysis (e.g. with preferably 28% hydrochloric acid for about 1 to 3 hours, such as about 2 hours);
- evaporating the reaction mixture and re-suspending the hydrolysed products in a weak acid such as acetic acid;
- determining the presence or absence of a product selected from a product according to Formula (IIIa), or according to Formula (IIIb)

(IIIa)

(IIIb)

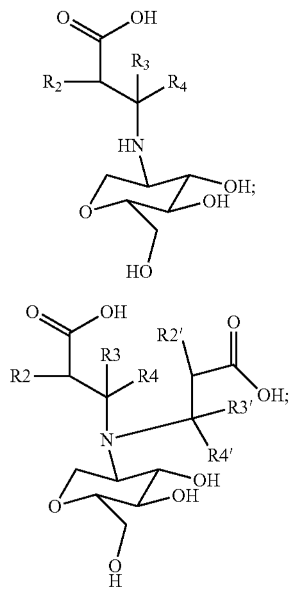

wherein $R_2$ to $R_4$ are as defined herein, $R_{2'}$ to $R_{4'}$ are as defined respectively as $R_2$ to $R_4$ herein and wherein the presence of a product of Formula (IIIa) and/or (IIIb) is indicative of cross-linked chitosan obtained by a method according to the invention.

According to another particular embodiment, in a method for identifying a cross-linked chitosan according to the invention, the presence or absence of a product according to Formula (IIIa) can be carried out for example by mass spectrometry electrospray analysis, wherein, for example, a peak with m/z=252.077 is indicative of the presence of a compound according to Formula (IIIa), in particular of Formula (II).

(II)

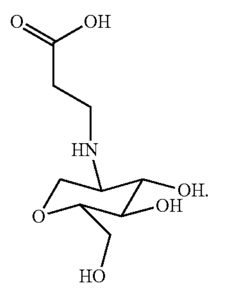

The method for identifying a cross-linked chitosan obtained from a method according to the invention is very useful since it allows to distinguish cross-linked chitosan obtained by a method according to the invention from cross-linked chitosan by other methods such as for example by a method described in Baoqiand et al., 2015, supra or El-sherbiny et al., 2009, supra.

Chitosan and Nanoparticles Thereof According to the Invention

The cross-linked chitosan according to the invention can be prepared from readily available starting materials according to a method of the invention. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimization procedures.

According to a particular embodiment, is provided a cross-linked chitosan and nanoparticles thereof obtained by a method of the invention.

According to another particular embodiment, is provided a cross-linked chitosan characterized by a lower viscosity than the starting chitosan. For example, for a 90% degree of deacetylation, 3.2% cross-linking and a concentration of 0.25% chitosan, a solution of nanoparticles according to the invention is 3 times less viscous than the starting chitosan, e.g. 2.4 cSt at 25° C. and 1.82 cSt at 37° C. for chitosan nanoparticles of the invention versus 7.5 cSt at 25° C. and 5.4 cSt at 37° C. for the corresponding starting chitosan.

According to a particular embodiment, pharmaceutically acceptable salts of the cross-linked chitosan of the invention comprise such as acetate, lactate, succinate, citrate, malonate, fumarate, maleate, a salt of malic acid, as well as other carboxylic, hydroxycarboxylic acids, in addition to this hydrochloride, phosphate, sulfate and other inorganic acids.

It is understood that the molecular weight of the cross-linked chitosan of the invention can be adapted in by the selection of the starting material and its choice will depend on the intended function of the nanoparticles of the invention and formulation thereof. For example, the desired nanoparticles composition degradation rate, the desired release rate of a bioactive agent optionally incorporated therein, the therapeutic condition to be treated will influence the choice of molecular weight for the chitosan as starting material.

In one embodiment, the molecular weight of cross-linked chitosan of the invention is comprised between about 2 kDa and 2 MDa.

In one further embodiment, the molecular weight of cross-linked chitosan of the invention for use in lubricating/filler composition may be chosen between about 2 kDa and 2, preferably from about 30 kDa and 1'000 kDa.

In another embodiment, the molecular weight of cross-linked chitosan of the invention for use in or as drug delivery system may be chosen between about 2 kDa and 2 MDa, preferably from about 30 kDa and 1'000 kDa.

Compositions

The invention provides pharmaceutical or therapeutic agents as compositions, or medical devices comprising thereof and methods for treating a subject, preferably a mammalian patient, and most preferably a human patient who is suffering a medical disorder and in particular cardiovascular conditions, such as cardiac arrhythmias, in particular atrial fibrillation and hypertension, joint pathologies and articular diseases, such as rheumatoid arthritis, osteoarthritis, spondyloarthritis, and traumatic events leading to cartilage, bone, ligament or synovial capsule damage, eye pathologies and injuries, such as dry eye syndrome, uveitis, glaucoma, corneal lesions, connective tissue disorders, such as lupus and polymyositis, skin/mucous membrane disorders or injuries, such as wounds, scars, psoriasis, acne, eczema, rosacea, burns of physical or chemical nature, in particular surgical wounds and sunburns, ulcers, haemorrhoids, periodontal and dental diseases, dural damage such as following accidental injury or brain and central nervous system surgery, malignant and benign neoplasms, carcinomas, sarcomas, lymphomas, and melanomas, postoperative complications such as fistulas and infections, tumors or vascular malformations, postoperative complications as fistulas and infections and tumor or a vascular malformation.

The invention provides compositions at least one cross-linked chitosan of the invention or composition thereof useful for human, veterinary or agricultural use.

In a particular embodiment, an agricultural composition according to the invention are useful as plant growth elicitor.

According to a particular embodiment, the cross-linked chitosan of the invention can be used for the preparation of self-assembled structures, molecular machines, delivery mechanisms, electronics, composite materials and lubricants.

In a particular embodiment, the invention provides a pharmaceutical formulation comprising at least one cross-linked chitosan of the invention or composition thereof for use as a medicament.

In another particular embodiment, compositions of the invention are parenteral formulations.

In a particular embodiment, compositions of the invention are injectable formulations, such as intra-articular, intra-arterial, intravenous, intra-synovial, intradermal, subdermal, submucosal, interstitial, intra-cranial, intra-ocular, intra-tumoral, intra-gastric, intestinal, anal, intra-peritoneal, and intramuscular formulations.

In another particular embodiment, compositions of the invention are oral formulations.

In another particular embodiment, compositions of the invention are topical formulations. In another particular embodiment, compositions of the invention are ophthalmic formulations.

Alternatively the invention provides compositions that can be used in another mammal thus humans for the same uses as described above.

The invention further provides compositions or medical devices useful for cosmetic, reconstruction surgery (e.g. tissue reconstruction), cell or biological tissue culture (e.g. stem cell culture), material science (e.g. surface coating such as implant coating, lubricant compositions, flocculant compositions), diagnosis (e.g. imaging compositions) applications. Those compositions further comprise respectively cosmetically acceptable carriers or cell or biological tissue culture nutrients.

Compositions according to the invention comprise soft tissue filler compositions, for example, dermal and subdermal fillers, comprising at least one cross-linked chitosan of the invention or nanoparticles thereof. Preparation of chitosan-based soft tissue filler compositions can be carried out for example as described in Grant et al., 2018, *Tissue Eng Part A.,* 24(13-14): 1091-1098. doi: 10.1089/ten.TEA.2017.0385. Epub 2018 Mar. 20.

In particular embodiment is provided nanoparticles of a cross-linked chitosan of the invention having a mean size ranging from about 5 and 100 nm.

Another aspect of the invention relates to a wound dressing comprising at least one cross-linked chitosan according to the invention.

According to a further particular aspect, the invention relates to a wound dressing comprising a permeating a matrix comprising a hydrocolloid, hydrogel, alginate, collagen, cellulose, foam or cloth.

Compositions of this invention may further comprise one or more pharmaceutically acceptable additional ingredient (s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and may be employed as solids, such as tablets or filled capsules, or liquids such as solutions, suspensions, ointments, emulsions, elixirs, or capsules filled with the same, films or gels, all for oral use. The compositions may also be formulated as a dry product for reconstitution with water or another suitable vehicle before use.

Compositions of this invention as liquid formulations including, but not limited to, aqueous or oily suspensions, solutions, emulsions, syrups, and elixirs.

Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in *The Science and Practice of Pharmacy* (*Remington: The Science & Practice of Pharmacy*), 22$^{nd}$ *Edition,* 2012, Lloyd, Ed. Allen, *Pharmaceutical Press*, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycolate. Wetting agents include, but are not limited to, sodium lauryl sulfate. Tablets may be coated according to methods well known in the art.

Agricultural compositions according to the invention comprise plant growth accelerators, seed germination enhancers, moisture and nutrient retention formulations, pesticide enhancers, prolonged forms and pheromone stabilizers, mucoadhesive forms of insecticides, arachnocides and anti-mollusk preparations.

According to a particular embodiment, is provided an agricultural composition comprising from about 0.001 to about 99% w/w of cross-linked chitosan of the invention, for example from about 0.05 to about 0.1% (w/w).

In another particular embodiment, the compositions or nanoparticles of the invention further comprise a bioactive agent, which is either dispersed in or covalently attached to the cross-linked chitosan composition.

In another particular embodiment, the compositions or nanoparticles of the invention are in the form of a bioactive agent delivery system.

In one embodiment the at least one bioactive substance may be present in an amount of between about 0.001 to 20 wt %, preferably about 0.01 to 10 wt % based on the total amount of the cross-linked chitosan composition or nanoparticle of the invention.

According to another aspect, compositions according to the invention comprise a cell or biological tissue culture medium comprising cross-linked chitosan or a composition thereof. This culture medium may further comprise cell nutrients such as glucose, vitamins, growth factors, metal ions and the like.

According to another aspect, compositions according to the invention comprise a biological tissue (endogeneous or exogeneous) or a synthetic or semi-synthetic material useful for repairing damaged tissues of the body such as epidermal, neurological, cartilage or bone tissues.

In another particular embodiment, is provided a method of preparation of a culture medium comprising a step of mixing cross-linked chitosan according to the invention with cell culture nutrients such as glucose, vitamins, growth factors, metal ions and the like.

In another particular embodiment, is provided a method of preparation of a reconstruction tissue comprising a step of combining cross-linked chitosan or a composition thereof according to the invention with materials, tissues or cells useful for repairing damaged tissues of the body such as stem cells or epidermal, neurological, cartilage or bone tissues. According to a particular aspect, compositions or nanoparticles of the invention can be useful, once loaded with a bioactive substance or agent, for administration and in situ release of the said active principle injection.

Mode of Administration

Compositions of this invention may also be administered in any manner by injection such as subcutaneous injections, intra-synovial, intra-arterial, intravenous, intraarticular, intramuscular, subdermal, submucosal, intra-ocular, intra-cranial, intra-gastric, intestinal, anal, intra-peritoneal, intra-tumoral and interstitial injections.

Compositions of this invention may be administered in any manner by oral route including to the mucosal surfaces of the oral cavity including the gingiva, the floor of the oral cavity, cheeks, lips, tongue, teeth.

Compositions of this invention may also be administered topically to the skin, various mucous or the eye.

Combination

According to one aspect, cross-linked chitosan or nanoparticles thereof of the invention or any suitable pharmaceutically acceptable thereof and pharmaceutical formulations thereof may be administered alone or in combination with at least one co-agent.

According to a particular aspect, co-agents according to the invention include antibiotics, nucleic acids, including gene constructs, antibodies and antibody fragments, toxins, cytostatics, antifungal agents, components of chemotherapeutic drugs, antihypertensive agents, antiarrhythmic substances, proliferation activating substances, hormones, cytokines, nitric oxide donors, and hydrogen sulfide donors.

The invention encompasses the administration of cross-linked chitosan or particles thereof of the invention and pharmaceutical formulations thereof to an individual simultaneously or sequentially with said at least a co-agent.

Cross-linked-chitosan or nanoparticles thereof according to the invention or a pharmaceutical formulation thereof that is administered simultaneously with said co-agent can be administered in the same or different composition(s) and by the same or different route(s) of administration.

The dosage administered, as single or multiple doses, to an individual will vary depending upon a variety of factors, including pharmacokinetic properties, patient conditions and characteristics (sex, age, body weight, health, and size), extent of symptoms, concurrent treatments, frequency of treatment and the effect desired.

Patients

In an embodiment, patients according to the invention are subjects suffering from cardiovascular conditions, such as cardiac arrhythmias, in particular atrial fibrillation and hypertension.

In another embodiment, patients according to the invention are subjects suffering from joint pathologies and articular diseases, such as rheumatoid arthritis, osteoarthritis, spondyloarthritis, and traumatic events leading to cartilage, bone, ligament or synovial capsule damage.

In another embodiment, patients according to the invention are subjects suffering from eye pathologies and injuries, such as dry eye syndrome, uveitis, glaucoma, corneal lesions.

In another embodiment, patients according to the invention are subjects suffering from connective tissue disorders, such as lupus and polymyositis.

In another embodiment, patients according to the invention are subjects suffering from skin/mucous membrane disorders or injuries, such as wounds, scars, psoriasis, acne, eczema, rosacea, burns of physical or chemical nature, in particular surgical wounds and sunburns, ulcers, hemorrhoids.

In another embodiment, patients according to the invention are subjects suffering from periodontal and dental diseases.

In another embodiment, patients according to the invention are subjects suffering from dural damage such as following accidental injury or brain and central nervous system surgery.

In another embodiment, patients according to the invention are subjects suffering from malignant and benign neoplasms.

In another embodiment, patients according to the invention are subjects suffering from postoperative complications as fistulas and infections.

In another further embodiment, patients according to the invention are subjects willing or requiring body parts volume enhancements or anatomical reshapes such as any enhancement/modification and/or increase of the volume of a body part for aesthetic or therapeutic reasons.

In another further embodiment, patients according to the invention are subjects suffering from a tumor, a vascular malformation or any other newly arising physical tissue or organ abnormality resulting in pain.

Use According to the Invention

According to a particular embodiment, due to its ability to spontaneously form nanoparticles the cross-linked chitosan of the invention is useful for various applications such as in vitro cell or biological tissue culture, as tissue fillers, for cosmetic, tissue and organoids engineering and material science applications.

In particular, according to one aspect, the cross-linked chitosan of the invention can be used as a carrier of pharmaceutical active ingredients (e.g. as drug delivery system, as a cell-penetration system (e.g. in gene therapy or for non-cell penetrating agents), as solubilizing agent, as capture agent: encapsulation of ingredients of interest within nanoparticles to generate suspensions for effective removal from solutions for example by switching from acid to alkaline pH).

According to another aspect, the cross-linked chitosan of the invention can be used as medical implants (e.g. coating of implants for improving biocompatibility, cell-containing regenerative medical implants) or materials (e.g. hemostatic materials).

According to another aspect, the cross-linked chitosan of the invention can be used as substrates for imaging agents (e.g. used in standard angiography (CT) and other emerging imaging modalities (e.g. EPR-based, NMR-based and X-ray-based)).

According to another aspect, the cross-linked chitosan of the invention can be used as substrates for cell culture (e.g. stem cells), cell culture medium, tissue engineering such as 3D printing of organoids, for separation/purification techniques, for cell transfection.

According to another aspect, the cross-linked chitosan of the invention can be used as nano-sized lubricants (e.g. after pyrolysis), dispersive agent for colloidal preparations or as flocculant.

According to another particular embodiment, is provided a use of cross-linked chitosan of the invention or a nanoparticle according to the invention or formulations thereof for the preparation of a delivery system, in vitro cell or biological tissue culture or of tissue engineering materials, such as neurosurgical, bone, cartilage, epidermal reconstruction tissues.

According to another particular embodiment, cross-linked chitosans or nanoparticles according to the invention or formulations thereof are useful for use in the prevention or treatment of a medical disorder, and in particular cardiovascular conditions, such as cardiac arrhythmias, in particular atrial fibrillation and hypertension, joint pathologies and articular diseases, such as rheumatoid arthritis, osteoarthritis, spondyloarthritis, and traumatic events leading to cartilage, bone, ligament or synovial capsule damage, eye pathologies and injuries, such as dry eye syndrome, uveitis, glaucoma, corneal lesions, connective tissue disorders, such as lupus and polymyositis, skin/mucous membrane disorders or injuries, such as wounds, scars, psoriasis, acne, eczema, rosacea, burns of physical or chemical nature, in particular surgical wounds and sunburns, ulcers, haemorrhoids, periodontal and dental diseases, dural damage such as following accidental injury or brain and central nervous system surgery, malignant and benign neoplasms, in particular carcinomas, sarcomas, lymphomas, and melanomas, postoperative complications such as fistulas and infections, tumors or vascular malformations or for the prevention and/or treatment of tissue degeneration and related disorders.

According to another further particular aspect, is provided cross-linked chitosans or nanoparticles according to the invention or formulations thereof for cosmetic use or for aesthetic and reconstructive surgery.

According to another further particular aspect, is provided cross-linked chitosans or nanoparticles according to the invention or formulations thereof for use in in vivo drug delivery.

According to a particular aspect, is provided the use of a nanoparticle according to the invention as a delivery system for at least one bioactive agent.

According to a particular embodiment, is provided a composition comprising at least one cross-linked chitosans or nanoparticles according to the invention which is useful in many medical applications such as delivery system for at least one bioactive agent or cell delivery system in tissue engineering, cell or biological tissue culture systems, and the like.

Examples illustrating the invention will be described hereinafter in a more detailed manner and by reference to the embodiments represented in the Figures.

EXAMPLES

The following abbreviations refer respectively to the definitions below:

DMF (Dimethylformamide); DMSO (dimethyl sulfoxide); MWCO (Molecular weight cut-off).

Example 1: Synthesis of a Chitosan of the Invention

Nanoparticles of a chitosan of the invention were synthesized as described in Scheme 1 above, wherein the starting materials used were the following:

a) Providing a Chitosan and Subjecting Said Chitosan to a Swelling Step in the Absence of Water (e.g. In a Aprotic Solvent)

450 g of dry chitosan (chitosan can be dried in vacuo over phosphorus oxide, in vacuo with moderate heat, azeotropic distillation with ethanol, acetonitrile, acetone or any other suitable solvent) are placed in a reactor in an inert atmosphere (e.g. purged with argon). This reactor is preferably a round-bottomed two-liter-flask equipped with a magnetic stirrer, a two-horned nozzle, into which a nozzle from the Drexel flask for purging with an inert gas (e.g. argon) and a dropping funnel with backpressure for adding reagents. 1'400 ml of an aprotic solvent (e.g. DMF) is then poured into the reactor and chitosan was allowed to swell for about 1 hour at room temperature.

In case undried chitosan is provided, 1'500 ml of an aprotic solvent (e.g. DMF) is poured into the reactor and chitosan is allowed to swell for 1 hour at room temperature, then, 300 ml of aprotic solvent (e.g. DMF) are distilled off in vacuo and then 200 ml of DMF are added to the dried chitosan into the reactor and the chitosan is allowed to swell for 1 hour at room temperature.

The reaction medium with swollen chitosan is then cooled to about 2-6° C. in an ice bath or with a bath connected to a thermostat for about 2-6° C. In the same bath, a 250 ml reactor (e.g. round bottom flask) with 100 ml dry DMF is also cooled. After cooling, the acylating agent is added to the aprotic solvent (100 ml of DMF), dropwise, with stirring and avoiding local overheating, while swirling the solvent. The solution of acylating reagent in DMF can warm up to about room temperature.

b) Acylating the Amino Groups of Said Chitosan with an Acrylic Compound of Formula (I) in the Absence of Water:

The solution of acryloyl compound prepared above is added to a suspension of chitosan obtained above within about 15 minutes with vigorous stirring, while preferably gently shaking the reactor (e.g. manually), while stopping the addition of acryloyl compound, since this allows to wash off the chitosan lumps with solvent sprays from the upper walls of the flask. After completion of the addition of the acryloyl compound solution, the dropping funnel is washed with a minimum amount of an aprotic solvent (e.g. DMF) of the order of 10-15 ml and this solution is added to the reaction medium. The cooling is removed and stirring is continued for another two hours with occasional shaking, allowing the reaction medium to warm to room temperature. After stirring, the flask is placed in an ultrasonic bath for about 15 minutes and the reaction mixture is subjected to ultrasonic treatment. During this time of ultrasonic exposure, only a slight heating of the reaction mixture occurs to no more than 30° C.

c) Subjecting the Acylation Product of Step b) to a Nucleophilic Addition Reaction (Aza-Michael Addition) in Presence of a Non-Nucleophilic Base:

After that, a non-nucleophilic base (e.g. triethylamine, diisopropylethylamine) is added in excess compared to the amount of acryloyl compound used under step b) to the reaction medium (e.g. through a dropping funnel) within about 15 minutes with vigorous stirring and periodic shaking. The mixture is left to mix overnight or about 15-18 hours at room temperature. Then, the reactor is placed in a bath with a temperature of about 55° C. and the mixture is stirred for about 6 hours. The reactor is removed from the bath and placed in an ultrasonic bath preheated to about 55° C. for about 15 minutes and the reaction mixture is subjected to ultrasonic treatment.

After ultrasonic treatment, the reactor is transferred to a rotary evaporator and the non-nucleophilic base is distilled off, if a volatile organic non-nucleophilic base is used. If a non-volatile base is used, then, the reactor is cooled to room temperature or lower temperature and an equivalent amount of acid (e.g. hydrochloric acid) is added with vigorous stirring. The pH of the resulting reaction medium is controlled to ensure achieving a neutral reaction medium.

d) Obtaining a Cross-Linked Chitosan of the Invention

The cross-linked chitosan is obtained under step c) in suspension in the aprotic solvent (e.g. DMF) with salts impurities. Therefore, the product is subjected to a purification step, for example by dialysis against deionized water. For example, this purpose, the reacting solution obtained under step c) is transferred to dialysis bags, closed with clamps and placed in containers with mixing deionized water on a magnetic stirrer. Dialysis can be monitored in different ways: for example by monitoring the salt contents through the measurement of the conductivity of washing liquids, or by monitoring the DMF content by UV absorption at a wavelength of less than 260 nm. If after the incubation of deionized water with a dialyzed product for 20 minutes, there are no significant differences either in electrical conductivity or in UV absorption, then the dialysis process is considered complete.

e) Optionally Obtaining a Cross-Linked Chitosan of the Invention in Dry State

It is possible to use a wet product obtained under step d) without drying it. However, it can be also dried, for example for the sake of formulation/storage or transport.

The purified product obtained under step d) is then dried. For example, drying can be carried out in a freeze dryer with preliminary freezing of the product; first in the presence of phosphoric anhydride or any suitable desiccant such as molecular sieves, potassium hydroxide and the like) at atmospheric pressure to absorb most of the liquid, and then in vacuum in the presence of phosphoric anhydride or any suitable desiccant or with preliminary evaporation on a rotary evaporator and repeated azeotropic distillation of water with ethanol and subsequent vacuum drying over phosphoric anhydride or any suitable desiccant.

Generally a yield of the method of the invention is about 90%. Losses are most likely associated with the entrainment of nanoparticles during drying, as well as losses during transfer from the reaction vessel, dialysis bags, since the priority of sterility and the absence of contamination is higher than the priority of yield.

f) Further a Cross-Linked Chitosan of the Invention in Dry State

Optionally, the purified cross-linked chitosan obtained under step c), step d) or step e) can be subjected to a saponification. For this purpose, the cross-linked chitosan obtained under step d) is placed in a reactor under inert atmosphere (e.g. purged with argon). 1'200 ml of deionized water are poured into the flask and an alkaline solution (e.g. NaOH in water) with a 20% molar excess relative to the amount of acryloyl compound used in approximately 100 ml of deionized water is added with vigorous stirring over about 15 minutes. It is advisable to gently shake the flask manually while stopping the addition of alkali, since this procedure allows you to wash off the chitosan lumps that got with solvent sprays to the upper walls of the reactor. After stirring, the reactor is placed in an ultrasonic bath and the reaction mixture is subjected to an ultrasonic treatment; after reaching a reaction mass of about 55° C., ultrasonic treatment is continued for another 2 hours at this temperature. After that, the obtained product can be either neutralized with an equivalent amount of acid, dialyzed or dried without neutralization, and after drying subjected again to at least one cycle of steps b) to c) (or d)/e). The use of more than one cycles of a sequence of steps b) to c) (or d)/e) allows increasing the saturation of the cross-linked chitosan with carboxyl functions.

Example 2: Example of Synthesis of Cross-Linked Chitosans of the Invention

Various cross-linked chitosans of the invention (CHI) has been synthesized according to the process describe therein, while varying the nature and the proportion of cross-linking agent. Examples are presented under Table 1 below.

In each case, 450 grams of chitosan is used as starting material. Examples 2a-2r and $C_1$, the acryloyl compound is acryloyl chloride (CAS registry number: 814-68-6). Examples 2t-2a1 the acryloyl compound is methacryloyl chloride (CAS registry number: 920-46-7). The reaction is carried out as described in steps a) to c) of the method of the invention. Examples 2 am-2as the acryloyl compound are different acryloyl chlorides.

TABLE 1

| CHI | Chitosan | Acryloyl compound | Cross-link/chitosan - Theoretical number of links or percentage of crosslinking |
|---|---|---|---|
| 2a | MW: 11.5 kDa DD: 62% | 4.250 g (20% excess to chitosan) | 1 |
| 2b | MW: 10.7 kDa DD: 91% | 4.570 g (20% excess to chitosan) | 1 |
| 2c | Same as 2a | 11.278 g | 9.8% of the amide/amine groups initially present in the chitosan macromolecule (4.9% generated at step b) and 4.9% generated at step c) |

TABLE 1-continued

| CHI | Chitosan | Acryloyl compound | Cross-link/chitosan - Theoretical number of links or percentage of crosslinking |
|---|---|---|---|
| 2d | Same as 2b | 12.112 g | Idem as 2c |
| 2e | Same as 2a | 71.35 g | totality of the amine groups |
| 2f | Same as 2b | 112.47 g | Idem as 2e |
| 2g | MW: 53.0 kDa DD: 70% | 0.922 g (20% excess to chitosan) | 1 |
| 2h | MW: 50.3 kDa DD: 91% | 0.972 g (20% excess to chitosan) | 1 |
| 2i | Same as 2g | 3.754 g | 3.2% of the amide/amine groups initially present in the chitosan macromolecule (1.6% generated at step b) and 1.6% generated at step c). |
| 2j | Same as 2h | 3.953 g | Idem as 2i |
| 2k | Same as 2g | 82.12 g | Idem as 2e |
| 2l | Same as 2h | 112.40 g | Idem as 2e |
| 2m | MW: 543.4 kDa DD: 60% | 90 mg (20% in excess of chitosan) | 1 |
| 2n | MW: 501 kDa DD: 93% | 98 mg (20% in excess of chitosan) | 1 |
| 2o | Same as 2m | 4.60 g | 4.0% of the amide/amine groups initially present in the chitosan macromolecule (2.0% generated at step b) and 2.0% generated at step c). |
| 2p | Same as 2n | 5.00 g | Idem as 2o |
| 2q | Same as 2m | 68.72 g | Idem as 2e |
| 2r | Same as 2n | 115.53 g | Idem as 2e |
| C1 | Glucosamine MW: 179.17 g/mol DD: 100% | 113.66 g | Idem as 2e |
| 2t | Same as 2a | 4.908 g (20% in excess of chitosan) | 1 |
| 2u | Same as 2b | 5.275 g (20% in excess of chitosan) | 1 |
| 2v | Same as 2a | 13.025 g | Idem as 2c |
| 2w | Same as 2b | 13.988 g | Idem as 2c |
| 2x | Same as 2a | 82.40 g | Idem as 2e |
| 2y | Same as 2b | 129.89 g | Idem as 2e |
| 2z | Same as 2g | 1.065 g (20% in excess of chitosan) | 1 |
| 2aa | Same as 2h | 1.122 g (20% in excess of chitosan) | 1 |
| 2ab | Same as 2g | 4.335 g | Idem as 2i |
| 2ac | Same as 2h | 4.565 g | Idem as 2i |
| 2ae | Same as 2g | 94.84 g | Idem as 2e |
| 2af | Same as 2h | 129.81 g | Idem as 2e |
| 2ag | Same as 2m | 104 mg (20% in excess of chitosan) | 1 |
| 2ah | Same as 2n | 113 mg (20% in excess of chitosan) | 1 |
| 2ai | Same as 2m | 4.233 g | Idem as 2i |
| 2aj | Same as 2n | 4.591 g | Idem as 2i |
| 2ak | Same as 2m | 79.37 g | Idem as 2e |
| 2al | Same as 2n | 133.42 g | Idem as 2e |
| 2am | Same as 2n | α,β-dimethyl acryloyl chloride (CAS [49651-33-4], M.W. 118.56 g/mol, 5.207 g | Idem as 2i |
| 2an | Same as 2n | 2-methylenedodecanoic acid chloride (CAS [52756-21-5], M.W. 230.77 g/mol, 10.135 g | Idem as 2i |
| 2ao | Same as 2n | (Z)-urocanic acid chloride (CAS [91788-89-5], M.W. 138.13 g/mol, 6.066 g | Idem as 2i |

TABLE 1-continued

| CHI | Chitosan | Acryloyl compound | Cross-link/chitosan - Theoretical number of links or percentage of crosslinking |
|---|---|---|---|
| 2ap | Same as 2n | (Z)-2-chloro-2-butenoyl chloride (CAS [56030-36-5], M.W. 138.98 g/mol, 6.104 g | Idem as 2i |
| 2aq | Same as 2n | Muconic chloride (CAS [58823-55-5], M.W. 179.00 g/mol, 3.931 g | Idem as 2i |
| 2ar | Same as 2n | (Z)-2-methylhept-2-en-6-ynoyl chloride (CAS [313217-54-8], M.W. 156.61 g/mol, 6.878 g | Idem as 2i |
| 2as | Same as 2n | Maleic anhydride (CAS [108-31-6], M.W. 98.06 g/mol, 4.307 g | Idem as 2i |
| 2at | Same as 2h | Same as 2j | Starting temperatures at step b) at step c) are −70° C. and reactions conducting at −20° C. during 10 days. |
| 2au | Same as 2h | 1/1000 part of same as 2j, 4 mg | The reaction is carried out as described at step b) at step c) of the General method, but in 1000 times less mass and in sealed 5 ml reactor. Starting temperature at step b) at step c) are −70° C. and reactions conducting at +150° C. during 30 minutes. |
| 2av | Obtained in 2f | | The reaction is carried out as described at step f). Under these conditions, the final amount of modified with propionic acid amino groups corresponds to half of the amine groups initially present in the chitosan macromolecule. |
| 2ax | Obtained in 2k | | Idem as 2av |
| 2ay | Obtained in 2r | | Idem as 2av |
| 2az | Obtained in 2av | 56.24 g of acryloyl chloride | The reaction is carried out as described at step b), at step c), at step f) Under these conditions, the 75% of the amine groups initially present in the chitosan macromolecule undergo modification with propionic acid. |
| 2ba | Obtained in 2ax | 41.05 g of acryloyl chloride | Idem as 2az |
| 2bb | Obtained in 2ay | 57.77 g of acryloyl chloride | Idem as 2az |
| 2bc | Obtained in 2r | | The reaction is carried out as described at step f), but saponification starts at 0° C. and continues 10 days at this temperature, amount of base is equimolar with acryloil chloride used. Under these conditions, the final amount of modified with propionic acid amino groups corresponds to half of the amine groups initially present in the chitosan macromolecule. |
| 2bd | Obtained in 2r | | The reaction is carried out as described at step f), but saponification starts at 0° C. and continues 30 minutes at 140° C. under pressure, amount of base is equimolar with acryloil chloride used. Under these conditions, the final amount of modified with propionic acid amino groups corresponds to half of the amine groups initially present in the chitosan macromolecule. |

TABLE 1-continued

| CHI | Chitosan | Acryloyl compound | Cross-link/chitosan - Theoretical number of links or percentage of crosslinking |
|---|---|---|---|
| 2be | Obtained in 2r | | The reaction is carried out as described at step f), but saponification starts at 0° C. and continues 10 days at 0° C., amount of base is 10 equivalents with acryloil chloride used. Under these conditions, the final amount of modified with propionic acid amino groups corresponds to half of the amine groups initially present in the chitosan macromolecule. |
| 2bf | Obtained in 2r | | The reaction is carried out as described at step f), but saponification starts at 0° C. and continues 30 minutes at 140° C. under pressure, amount of base is 10 equivalents with acryloil chloride used. Under these conditions, the final amount of modified with propionic acid amino groups corresponds to half of the amine groups initially present in the chitosan macromolecule and some saponification of acetyl groups occur. |
| 2bg | Same as 2a | 143 g of acryloyl chloride | The reaction is carried out as described at step b). Under these conditions, the totality of the amine groups initially present in the chitosan macromolecule undergo modification with acrylic acid forming acroloyl amides containing double bond. |
| 2bh | 2000 kDa, DD 10% | 3.278 g of acryloyl chloride and 10% solution of LiCl in N,N-dimethylacetamide as a solvent | The reaction is carried out as described at step b) and at step c). Idem 2i. |

Example 3: Characterization of the Nanoparticles of a Chitosan of the Invention A sample of 3.2% cross-linked 501 kDa chitosan (Example 2i) prepared as described above was adsorbed for 30 seconds on a formvar/carbon coated copper grid, and stained with uranyl acetate for 5 seconds. A micrograph of the stained material was then obtained using a Jem1400 transmission electron microscope (Jeol) and a Veleta camer (SIS, Germany) (FIG. 1A) which shows that the bulk of the preparation consists of globular particles with an approximate diameter of 15 nm, similar in size to small mammalian viruses. Some larger particles can also be observed, with diameters in the 60-80 nm range, corresponding to that of medium-sized viral particles.

Figure 2:
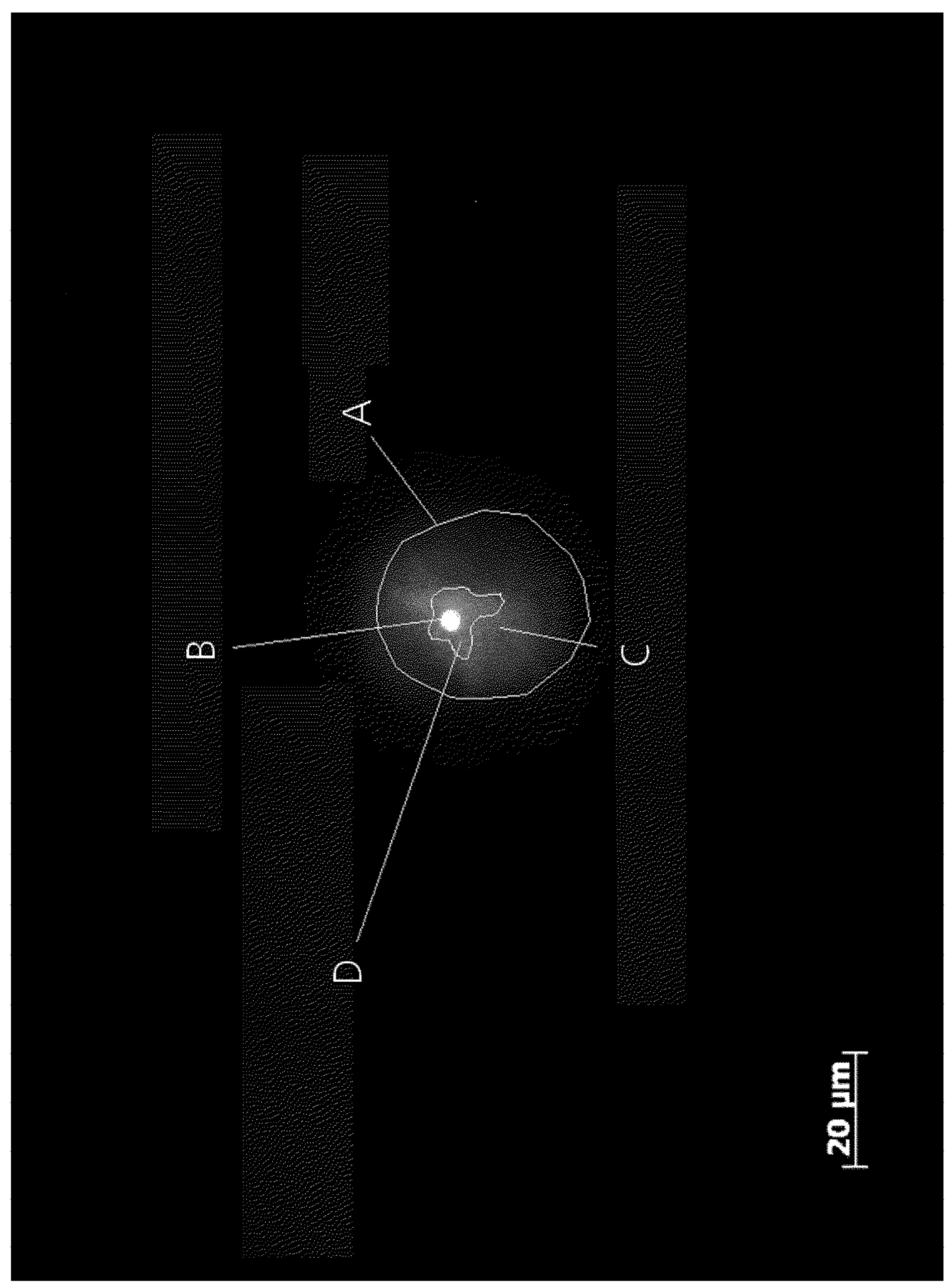
FIG. 2 shows the internalization of cross-linked chitosan nanoparticles of the invention (Example 2i) in murine leukocytes as measured by fluorescence microscopy as described in Example 4. A: Leukocyte boundary; B: Nuclear DNA (Hoechst 33258, intense blue fluorescence); C: Endocytosed FITC-labeled crosslinked chitosan (Green fluorescence); D: Mixed blue/green fluorescence (blue: background non-specific and/or non-nuclear DNA in the cytoplasm; green: endocytosed FITC-labeled crosslinked chitosan).
Figure 3:
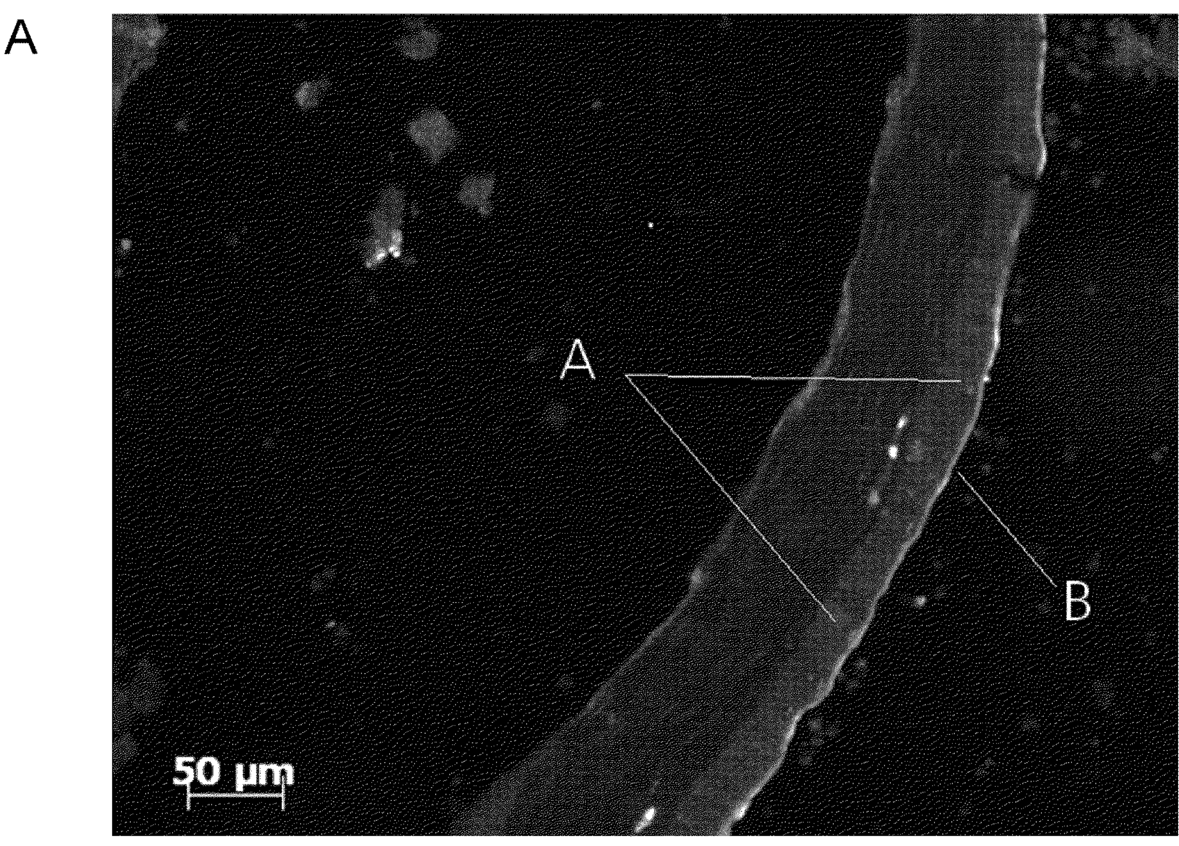
FIG. 3 shows the internalization of cross-linked chitosan nanoparticles of the invention (Example 2i) (B) in murine cornea compared to standard chitosan (A) which remains on the surface of the cornea by FITC-FAM fluorescence as described in Example 4. A: Cornea; B: Chitosan (bright green fluorescence).
Figure 3:
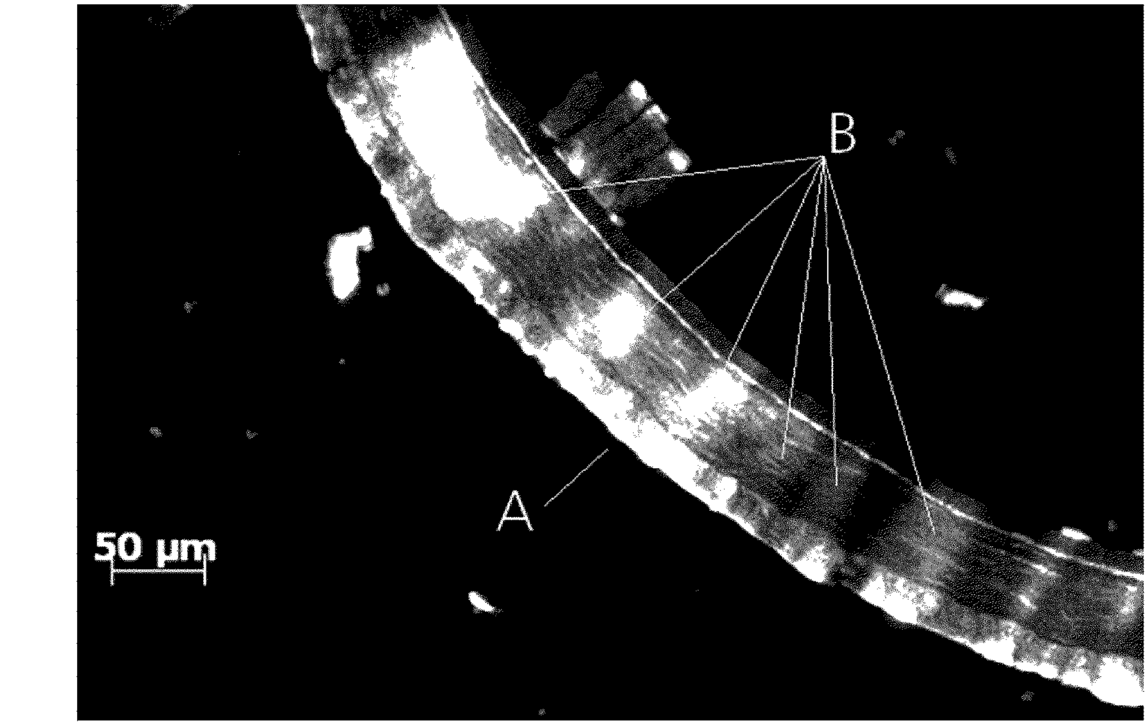
Figure 4:
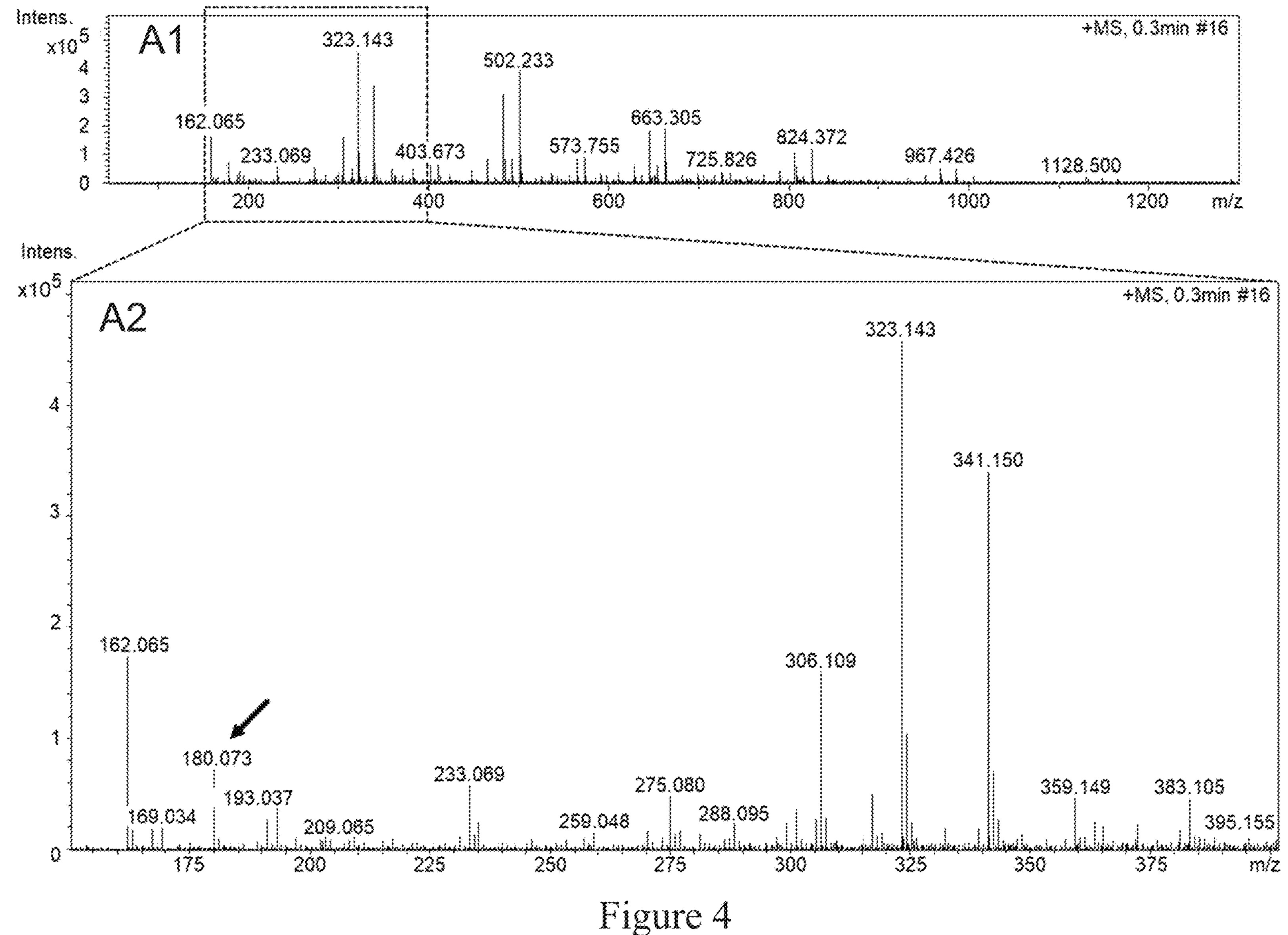
FIG. 4 represents the mass spectrometry analysis of a comparative non-cross-linked standard chitosan (A1: total ion current for positive ions) and (A2: region of ions of interest (lower m/z ratio)); of a cross-linked chitosan of the invention (B1: total ion current for positive ions and B2 (region of ions of interest (lower m/z ratio)) as described in Example 3.
Figure 4:
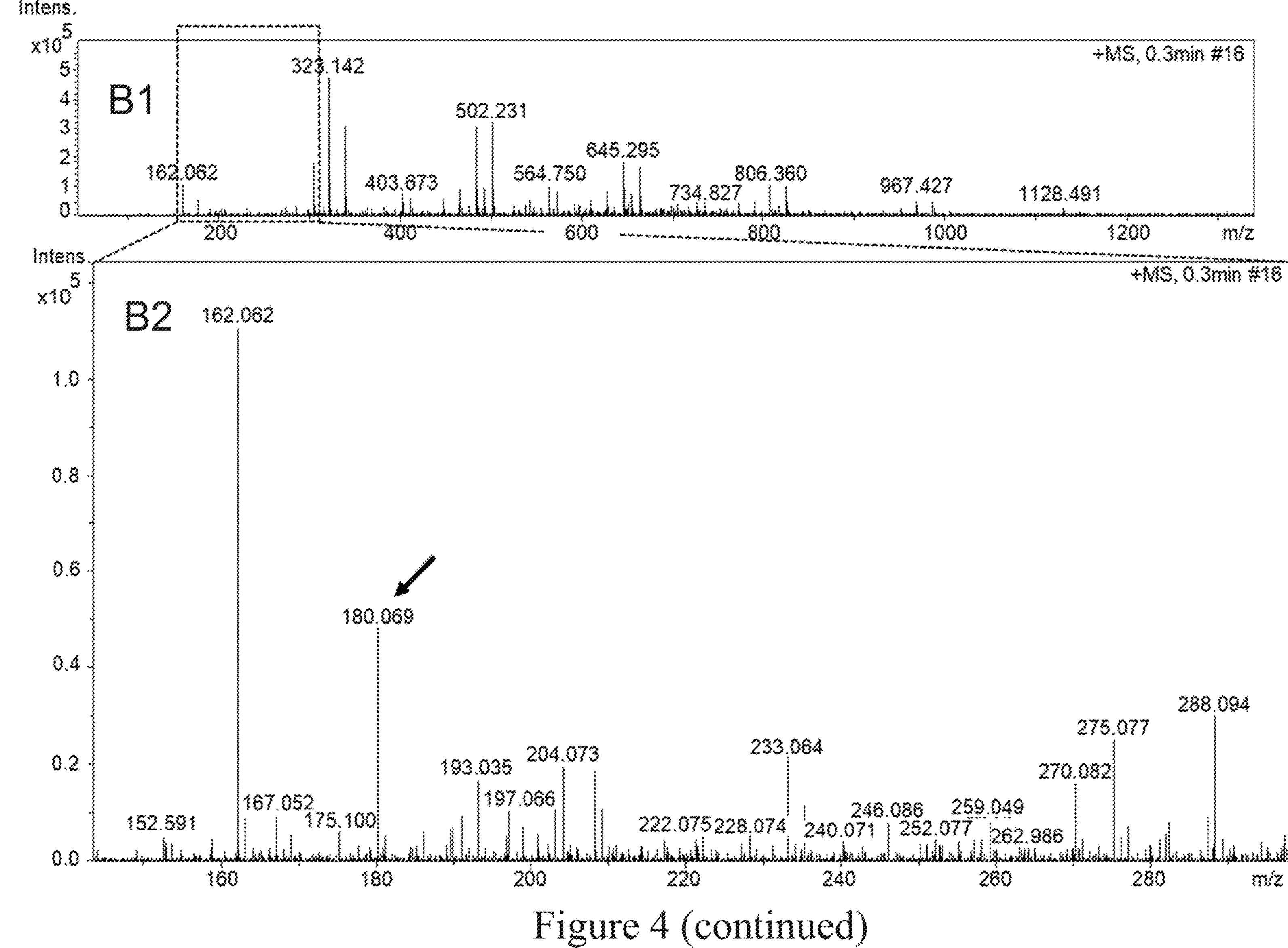

Further, dried films of standard linear chitosan (MW: 501 kDa, 93% DD) (Bioavanta) and of a cross-linked chitosan according to the invention made from the same chitosan (Example 2i) were obtained by pouring a solution of 2% chitosan in 1% aqueous succinic acid into a Petri dish, thereby forming a 1 mm layer which is then dried in vacuum over phosphoric anhydride to constant weight at room temperature and those films were then analyzed with a «Solver Bio» atomic force microscope (NT-MDT, Zelenograd, Russia), in semi-contact mode. The three-dimensional representation of a 100 μm×100 μm film surface area of the standard chitosan sample (MW: 501 kDa, 93% DD) shows that the surface is smooth, with the linear chitosan polymers probably arranged collinearly (FIG. 1B1), while the surface area of the corresponding cross-linked chitosan sample of Example 2i is rugged, with "peaks" and "valleys", formed by agglomerations of globular structures (FIG. 1B2). FIGS. 1B3 and B4 visualize by atomic force microscopy films, comprising bacterial nanocellulose imbibed with 1% w/w cross-linked chitosan according to the invention solution in water. AFM measurements were performed in semi-contact mode on a Solver Next scanning probe microscope (NT-MDT, Russia) under standard room conditions in air (T=26° C., RH=15%). ScanAsyst-AIR AFM probes (Bruker, USA) with a beam-cantilever stiffness of ~0.4 N/m with a resonance frequency of ~70 kHz and a nominal radius of curvature (sharpness of the AFM probe) of 2 nm were used for optimal pressure force (SetPoint). All measurements were performed at a scanning speed of 0.5 Hz and a resolution of 512×512 points. Subsequent processing was performed in the ImageAnalysis 3.5 program by subtracting the inclined plane and removing measurement defects ("sticking"). Analysis of the obtained FIGS. 1 B3 and B4 revealed globular structures uniformly distributed on the sample surface (FIGS. 1 B3 and B4), with a 20 nm average diameter of globules, which corresponds to the size of small viruses, such as Caliciviridae, Picornaviridae, Parvoviridae. The presence of the structures observed in AFM is confirmed by the data of earlier transmission electron microscopy (FIG. 1A).

The structural differences between standard chitosan (negative control) and a cross-linked chitosan (Example 2i) of the invention and a cross-linked glucosamine (Comparative Example C1) (positive control) are further investigated under inert atmosphere (e.g. Argon) by a method of a reflux acid hydrolysis which allows the analysis of low molecular weight substances in an accurate manner for identifying a marker substance formed only in the case of a successful cross-linking as follows:

The samples (100 mg each) are added with vigorous stirring to a solution of 1 ml of acetyl chloride in 5 ml of methylene chloride cooled to −20° C. The mixture is then heated to 0° C. and kept under vigorous stirring for 30 minutes. Diisopropylethylamine (1 ml) is added and the mixture is warmed to room temperature and maintained with vigorous stirring for another 30 minutes. The neutralization of the resulting hydrochloride, subsequently will allow to wash with water all the substances that interfere with the analysis and also, the presence of a non-nucleophilic strong base allows acetylation to be carried out as fully as possible. All solvents are carefully evaporated in vacuo and the residue is washed three times with 1 ml water samples. Wash water is discarded, and 10 ml of 28% hydrochloric acid is added to the solid precipitates and refluxed for 2 hours. The reaction mixtures are carefully evaporated under vacuum and the residues (approx. 100 mg) are re-suspended in 100 ml 2% aqueous acetic acid. At that point the samples are ready. Complete hydrolysis of the polymer to glucosamine and a glucosamine derivative has occurred then under the present conditions. Therefore, since substance of Formula (II) is not found in natural chitin and chitosan, it can only be obtained by the reaction of aza-Michael with the remainder of acrylic acid and therefore the detection of such substance can be used for identifying a cross-linked chitosan made by a method according to the invention.

If any acryloyl chloride (e.g. the acid chloride of any acrylic acid used for the cross-linking step according to the invention) of Formula (I) is used as a cross-linking reagent (for example for 2i example), after preliminary sample preparation (e.g. acetylation, washing), the reflux acid hydrolysis of the obtained polymers which leads to not only hydrolysis of the glycoside bonds between glucosamine units, but also of the amide bonds of both acetylglucosamine and the ones created during acylation with a cross-linking agent (e.g. activated for acylation substituted or non-substituted acrylic acid derivatives) will lead to the formation of the following derivative of glucosamine and propionic acid of Formula (IIIa):

(IIIa)

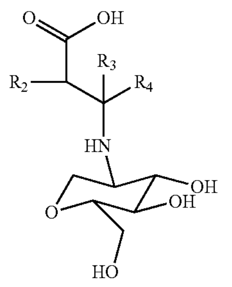

wherein $R_2$ to $R_4$ are as defined in the present application, in particular the following derivative of glucosamine and propionic acid of Formula (II) if non-substituted, acylation-activated acrylic acid is used:

(II)

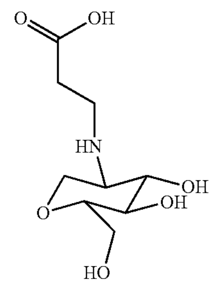

This substance is hydrolytically stable and must be present in the mixture if cross-linking had initially occurred. Similar derivatives (IIIa) are formed if other cross-linking reagents are used. In case of high degree of cross-linking carried, the detection of derivatives of Formula (IIIb) can be used for identifying a cross-linked chitosan made by a method according to the invention (IIIb)

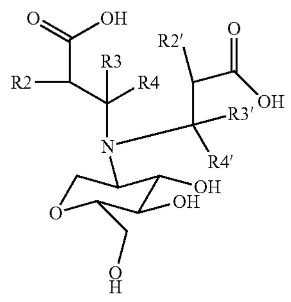

wherein $R_2$ to $R_4$ are as defined herein, $R_{2'}$ to $R_{4'}$ are as defined respectively as $R_2$ to $R_4$ herein, wherein $R_{2'}$ to $R_{4'}$ can be identical respectively to each corresponding $R_2$ to $R_4$ or different if acrylic compounds of Formula (I) used in subsequent sequence of steps b) to c) in a method of the invention are different from those used in the first sequence.

To support the presence of cross-linking in a product resulting from a method of the invention, the samples solutions prepared as described above are used in mass spectrometric analysis (Broker Daltonics TOF 180 mkl/h, tune_low.m, ES pos. scan, N2-41/min, 190 C, Nb.=0.4, Spectra time 1s) directly, without prior chromatography. In the mass spectra in the region of ions of interest (lower m/z ratio) for both comparative standard chitosan (Fig. A2) and the cross-linked chitosan of the invention (Fig. B2), a glucosamine-specific peak is observed (m/z=180.073), reflecting the presence of intact residues of amino glucose. However, for the cross-linked chitosan of the invention, a new peak with m/z=252.077 appears (Fig. B2), corresponding to the product of Formula (II) resulting from the alkylation of amino glucose with propionic acid. In this example, peak intensity is low, reflecting the low percentage of crosslinking of the sample (3.2% crosslinking as determined by the reaction conditions 2i. This is a characteristic peak which supports successful chitosan crosslinking according to the method of the invention. It was present in all samples resulting from method of the invention conducted under various appropriate conditions as described in Table 1 above (including the comparative glucosamine positive control) and absent in all chitosans and chitins tested.

Figure 5:
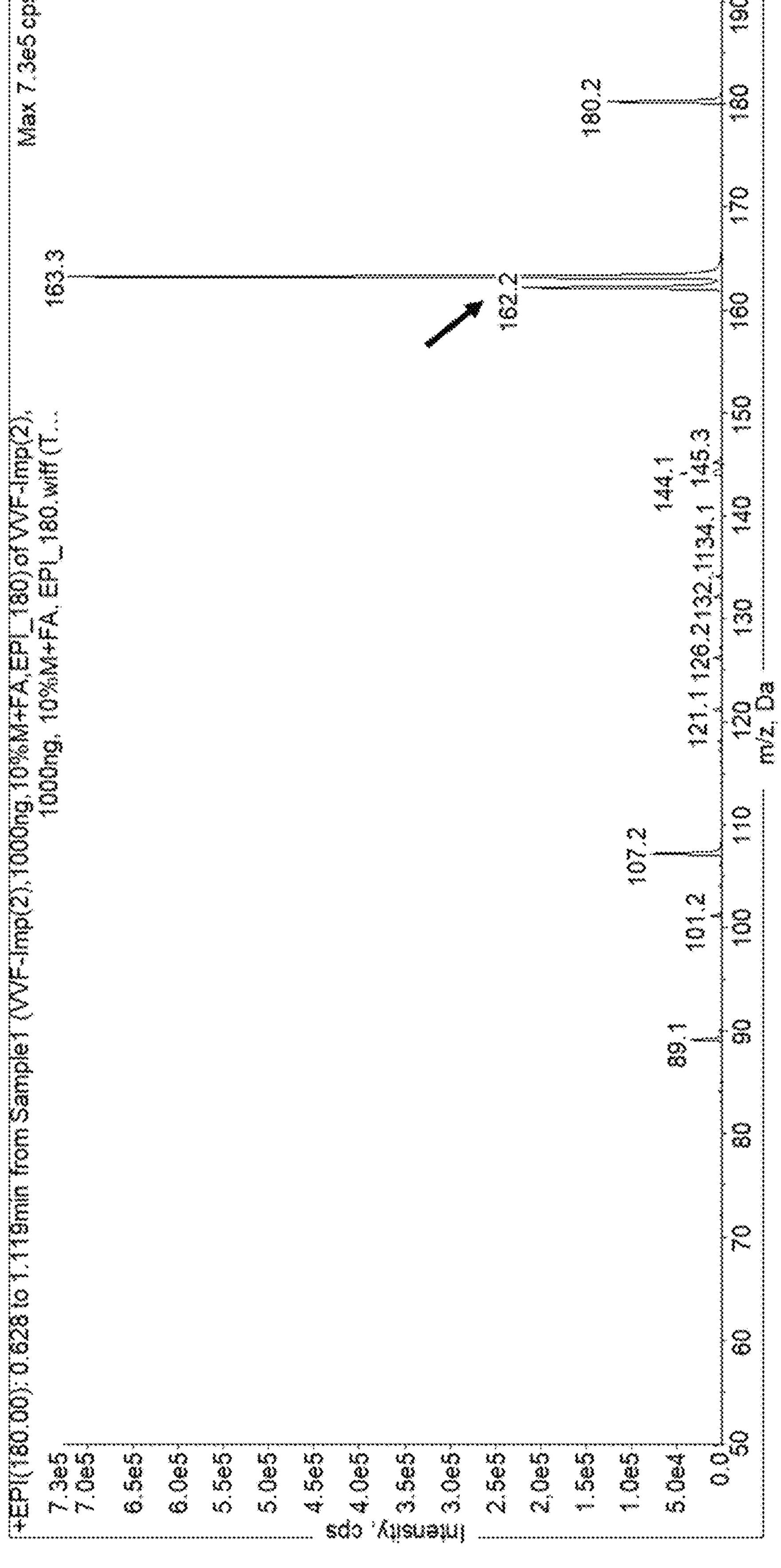
FIG. 5 represents the spectra resulting from collision studies of the m/z=180 compound at an impact energy of 5V (A) and 15 V (B) and for the m/z=252 compound at an impact energy of 5V (C) and 15 V (D) and resulting from the hydrolysis of egg lysozyme (E) as described in Example 3.
Figure 5:
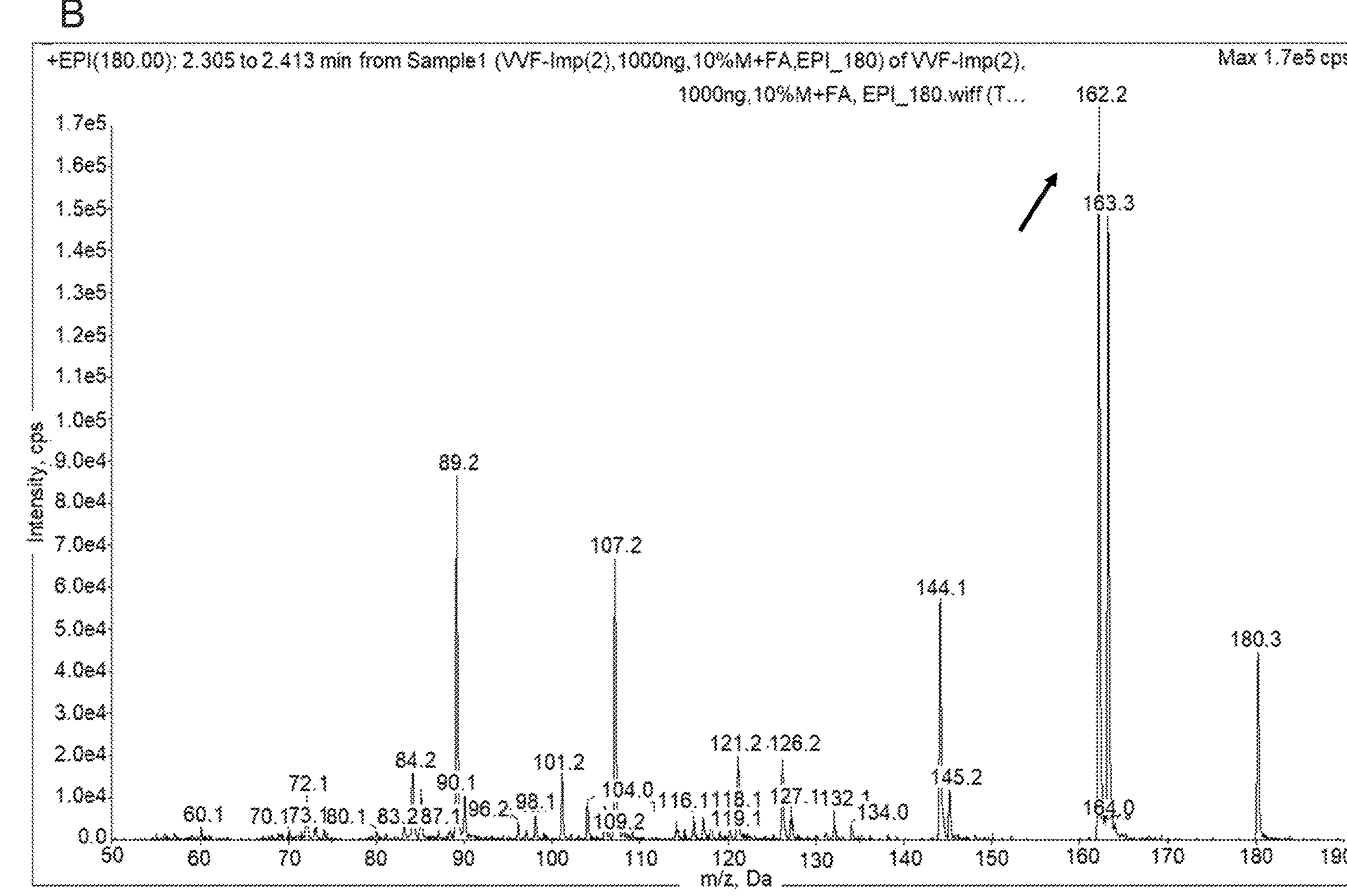
Figure 5:
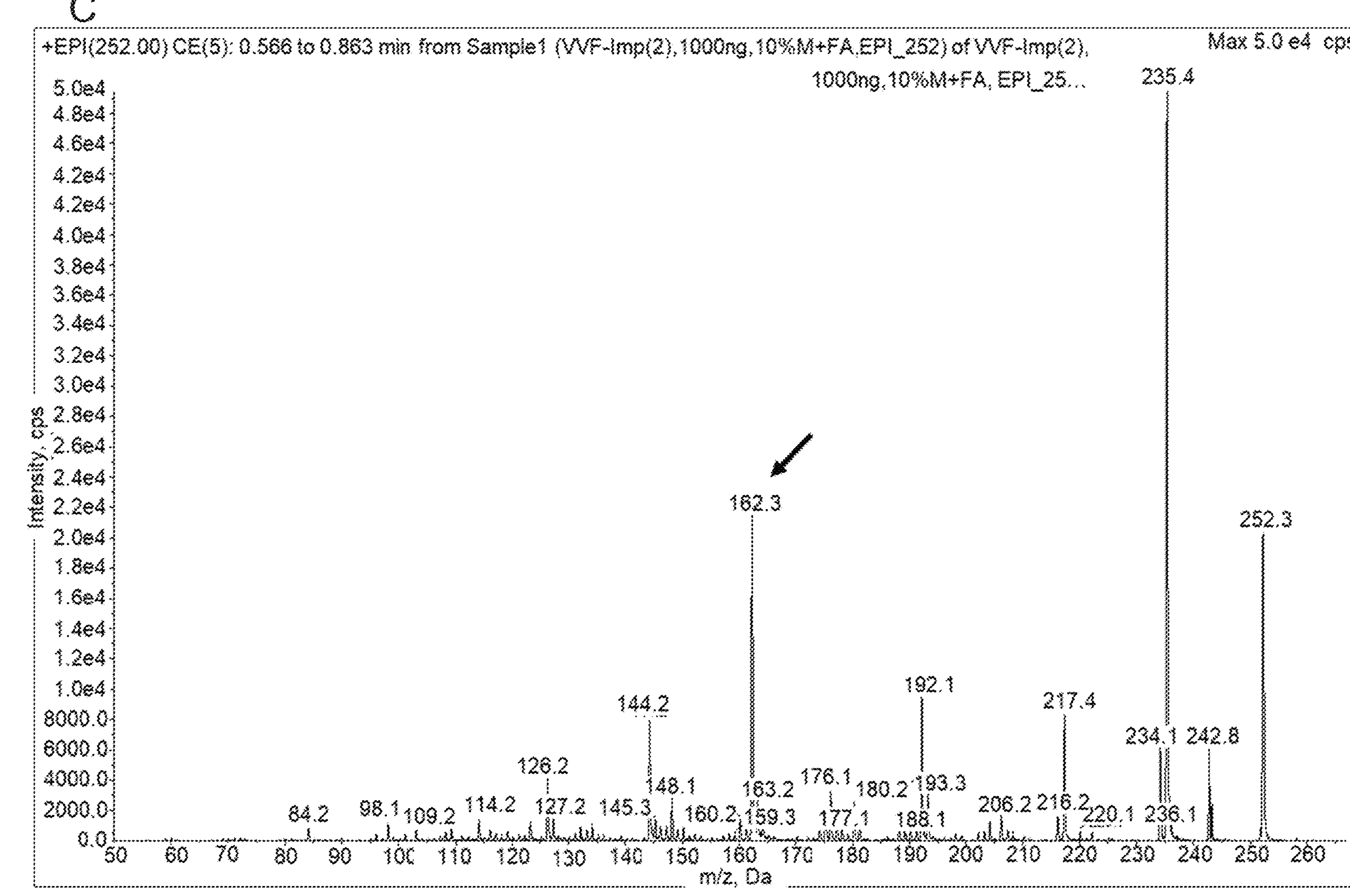
Figure 5:
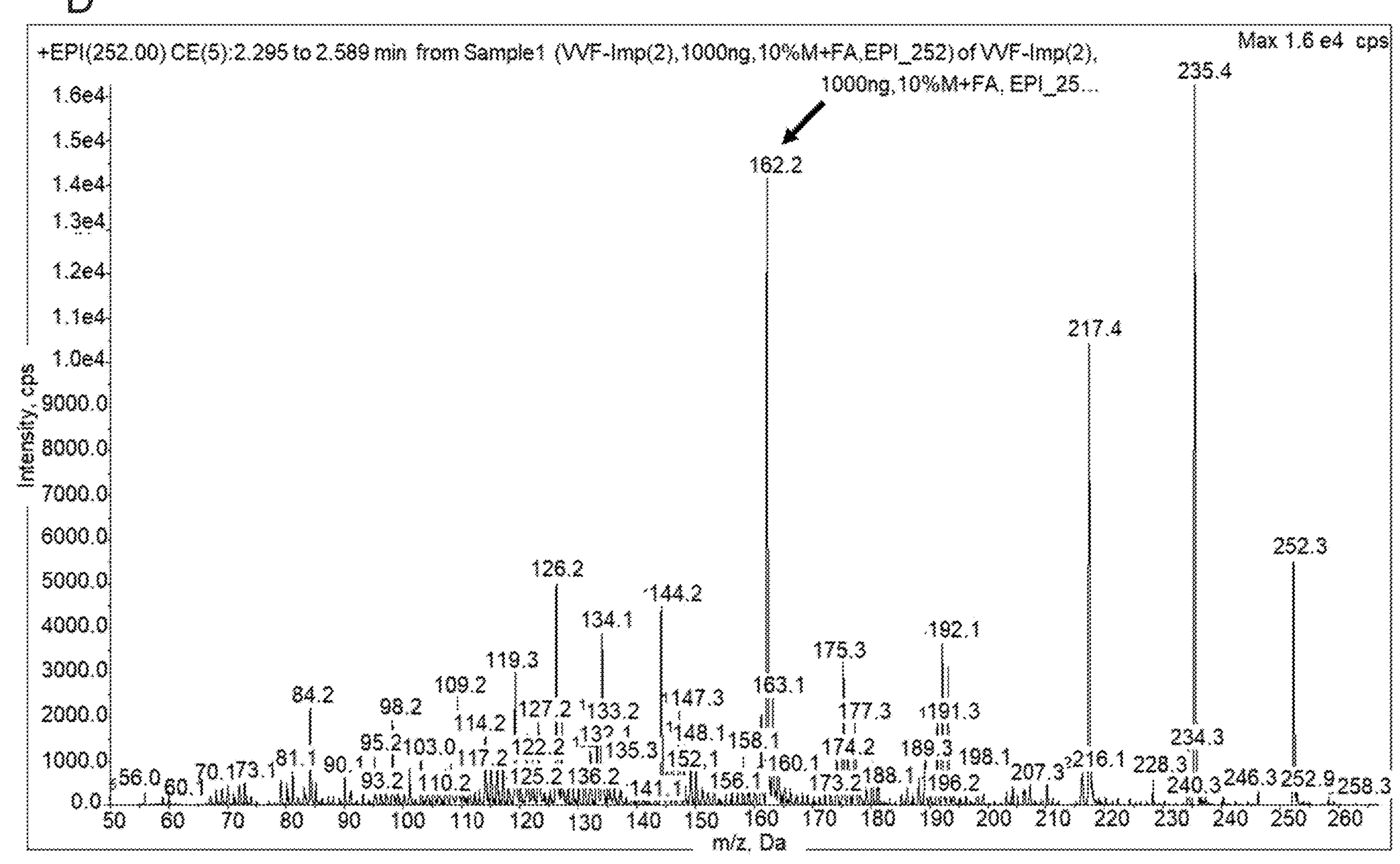
Figure 5:
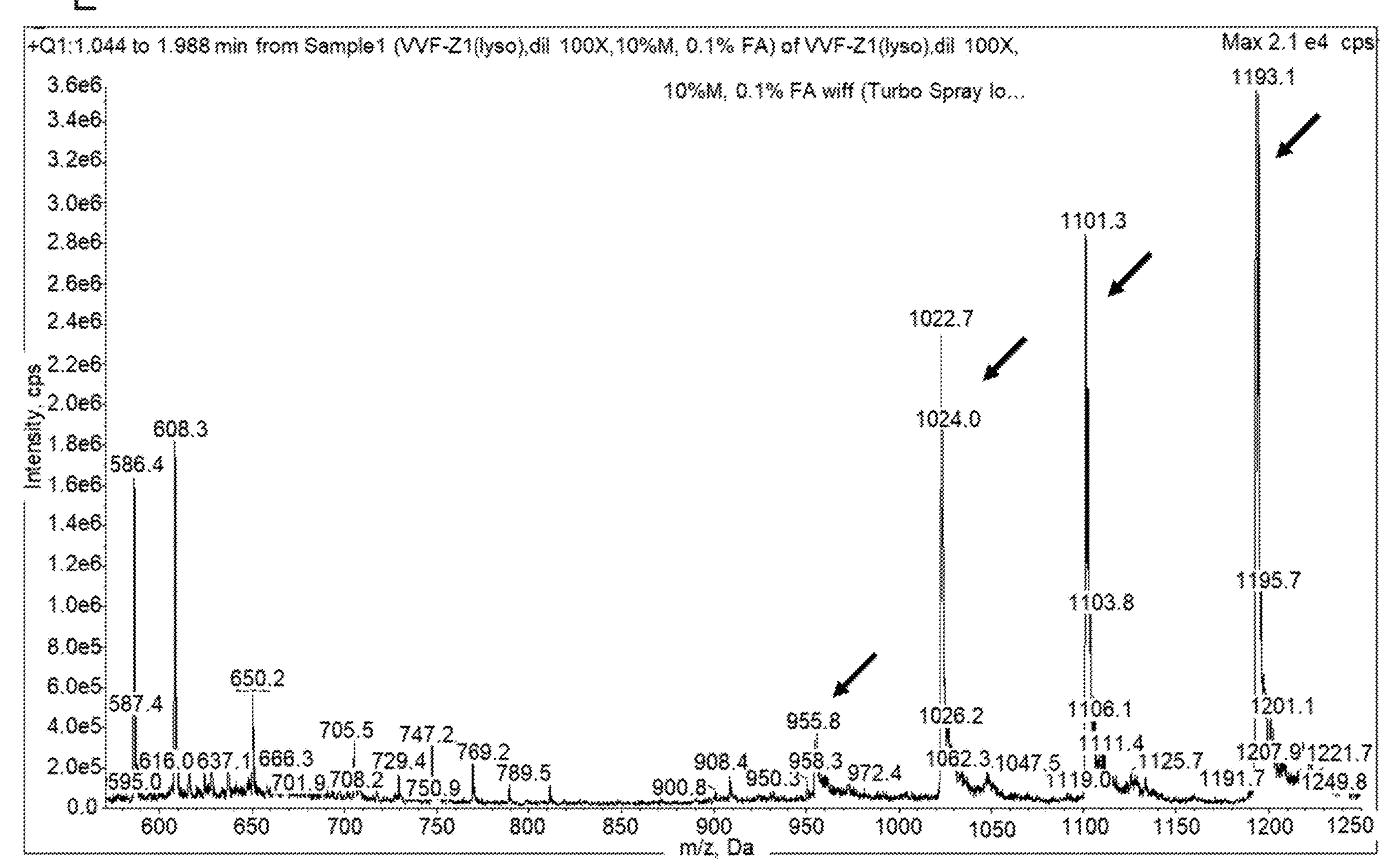

In order to confirm the attribution of the m/z=180 and m/z=252 peaks to glucosamine and the compound (II), collision studies were conducted at different impact energies (AB SCIEX Triple Quad™ 3500) (5V and 15V). In this case, the pretreated dry residues (after hydrolysis, the reaction mixtures are evaporated under vacuum) were dissolved in an aqueous solution containing 10% methanol and 0.1% formic acid. Upon fragmentation at higher impact energy (Sciex instrument) of the m/z=180 compound, a spectrum with water loss (−18 m/z, −2*18 m/z, −3*18 m/z) is observed (FIGS. 5A and 5B). With an increase in the energy of collisions, the intensity of the peaks of water loss also increases. This phenomenon is characteristic of carbohydrates. A similar picture is observed for ion the m/z=252 compound (FIGS. 5B and 5C). However, as a derivative of a carbohydrate, it can be more stable with respect to water losses, at the same collision energies. Accordingly, the observed relative intensities of the peaks representing water losses are lower.

The stability of the 3.2% cross-linked 501 kDa chitosan of the invention (Example 2i) prepared as described above was monitored by mass spectrometry after the addition of 500 μl of a solution of egg lysozyme at a concentration of 10 mg per ml in sodium acetate buffer (pH 5.5) to 5 mg of the invention. The mixture was incubated on a shaker at 37° C. for 7 days until no further changes in the mass spectrum could be observed anymore. At that stage, the mass spectra revealed a characteristic "comb"-like pattern of high molecular weight compounds: regularly interspersed peaks with a regularly increasing intensity at 955-958, 1023-1024, 1101-1104, 1193-1196 m/z ratios. The peaks correspond to the same fragments differing by unit of charge. For the given masses, the ion charges are +15, +14, +13 and +12. The mass of the main fragment is 14'305 Da. Similar results were obtained on samples incubated for longer periods, up to 3 weeks. This demonstrates that hydrolase, responsible for the hydrolysis of chitosan and its derivatives both in egg white lysozyme and in the tissues of warm-blooded animals, is able to hydrolyze cross-linked chitosan only to rather large fragments with a mass of about 14 kDa. Therefore, this suggests that the higher molecular weight and deacetylated chitosan is used to prepare nanoparticles, the more stable it would be to enzymatic hydrolysis.

Therefore, those data support a high difference in structure between the cross-linked chitosan of the invention forming nanoparticles and the standard chitosan used as starting material. Further, a method based on the detection of a substance of Formula (II) or related substances is highly sensitive and highly specific in the detection of nanoparticles obtained by a method of the invention.

Example 4: Cell Internalization of the Nanoparticles of a Chitosan of the Invention The ability of the nanoparticles of a chitosan of the invention to be internalized by cells has been tested as follows by fluorescence microscopy, using fluorescein isothiocyanate (FITC) and 5-(and 6-)carboxyfluorescein (FAM)-labeled chitosan permeation inside murine cornea.

Fluorescein-labeled cross-linked chitosans were prepared using either standard, initial chitosan with a molecular weight of 501 kDa and a degree of deacetylation of 93% or 3.2%, cross-linked chitosan according to the invention (Example 2p). DMF (1 ml) pre-chilled in an ice bath, was added to both chitosans (100 mg) in Eppendorf tubes, and the suspension left to swell for 1 hour. Solutions of 2.85 mg Fluorescein-5-Isothiocyanate (FITC) or 5-(and 6-) carboxyfluorescein succinimidyl ester (NHS-Fluorescein) in 250 μL of DMF were then added in an ultrasonic bath filled with ice water and subjected to ultrasonic treatment. The first twenty minutes the temperature in the bath was maintained at 0° C., and then the bath was heated to 40° C. and the reaction was carried out at this temperature for 100 minutes. The contents of the tubes were transferred to 12-14 kDa dialysis tubes and dialyzed against water. After 20 dialysis procedures against 100 ml of water, 50 mg of succinic acid was added to each dialysis tube, chitosans were dissolved and the dialysis procedure was repeated. The resulting solutions were lyophilized and subsequently resuspended to yield 0.25% solutions.

Murine leukocytes were incubated with these solutions for 4 hours at 37° C., stained with DNA-specific dye (Hoechst 33258) and analyzed by fluorescence microscopy. The fluorescence analysis (FIG. 2) shows green fluorescence (C) is uniform throughout the cytoplasm, indicating that FITC-labeled crosslinked chitosan is inside the cell and therefore has been endocytosed (simple association of the labeled chitosan with the cell membrane would have created a fluorescent ring at the boundary of the cell (A). The blue fluorescence observed outside of the nucleus (D) may be caused by the initiation of apoptosis The same solutions (0.25%) of fluorescein isothiocyanate (FITC) and 5(6)-carboxyfluorescein (FAM)-labeled were applied to the eyes of CBA mice (one drop per eye). After 6 hours, the experimental animals were sacrificed, and the eyes were fixed in formalin, stained as described in Stradleigh et al., 2015, *Prog Retin Eye Res.*, 48: 181-202 and analyzed by fluorescence microscopy. It is observed that whereas standard chitosan concentrated preferentially on the surface of the cornea and sclera (FIG. 3A), chitosan nanoparticles of the invention (bright green fluorescence) penetrated the cornea deeply, in a uniform manner (FIG. 3B).

Those data support that the cross-linked chitosan nanoparticles of the invention would be useful for increasing the cell penetration abilities of poorly cell-penetrating (hydrophilic) or cell non-penetrating (large molecules) active ingredients either to intracellular locations through nanoparticle-mediated endocytosis and/or possibly across cells through nanoparticle-mediated transcytosis.

Example 5: Biocompatibility of the Nanoparticles of a Chitosan of the Invention Biocompatibility of a cross-linked chitosan of the invention (Example 2i) was assessed in in vitro cultures of human bone marrow mesenchymal stem cells (MSCs), collected from healthy donors through bone marrow aspiration as described in Bieback et al., 2008, *Transfus Med Hemother.*, 35(4): 286-294, doi: 10.1159/000141567 in order to assess its possible influence on the culture and growth of MSCs.

MSCs were isolated as described in Bieback, et al., 2008, supra through 1,077 g/ml density gradient centrifugation, followed by 2 washes and grown in DMEM growth medium containing 10% Mesecult fetal serum, 1-glutamine and antibiotics. The purity of the culture was verified using flow cytometry. The cultured MSCs displayed the following phenotype: CD44+/CD73+/CD90+/CD105+/CD34−/HLA-DR− with a demonstrated capacity for chondrogenic, osteogenic and adipogenic differentiation upon addition of specific media as described in Ciuffreda et al., 2016, *Methods Mol Biol.* 2016; 1416: 149-58. doi: 10.1007/978-1-4939-3584-0_8. The study employed cells at 4 passages.

The walls of 25 $cm^2$ culture dishes were covered with a film of the cross-linked chitosan, the dishes were dried washed twice with growth medium and seeded with cells. Untreated culture dishes of the same size were similarly seeded for comparison. The presence of the cross-linked chitosan on the plastic walls of culture dishes did not interfere with cell attachment and cell growth. Within 3-4 hours after inoculation, the cells spread and adopted their characteristic spindle-like shape. The growth rate was somewhat slower in cross-linked chitosan-treated dishes. Confluency was reached after 48-56 hours in standard culture dishes and after 68-76 hours in cross-linked chitosan-treated culture dishes.

In conclusion, cross-linked chitosan of the invention sustains the growth and proliferation of human bone marrow mesenchymal stem cells, albeit at a lower efficiency than under standard conditions.

Example 6: Use of a Chitosan of the Invention for Applications in Agriculture The usefulness of a cross-linked chitosan of the invention (Example 2i) was tested on Spring wheat seeds as follows. Suspensions in water of the cross-linked chitosan of the invention were prepared at two different concentrations, seeds were immersed in the suspensions and each experiment included the following groups of seeds, depending on the applied treatment:

(A) Control (No treatment of seeds);

(B) Treatment with 0.1% (w/w) cross-linked chitosan, (C) Treatment with 0.05% (w/w) cross-linked chitosan.

Assessment of the Growth-Promoting Effects at the Initial Stages of Organogenesis After a 24-hour-treatment, seeds were laid on a humid substrate (filters with a cotton layer) in Petri dishes (12 seeds per dish, in quadruplets), natural light, t=+20-22° C. Germination energy was determined as described in Domin et al., 2020, Sustainability 2020, 12(1), 46 and measured after 1 and 3 days after contacting the humid substrate and germination capacity (number of germinated seeds divided by the total number of tested seeds minus the empty ones) was determined after 7 days after contacting the humid substrate. Growth indicators at the initial stages of organogenesis were recorded after 3 days (length of roots of each seedling, total length of seedlings) and after 7 days (number of roots per seedling, length of seedlings, total mass of roots and shoot per seedling, and mass of each root) after contacting the humid.

Figure 6:
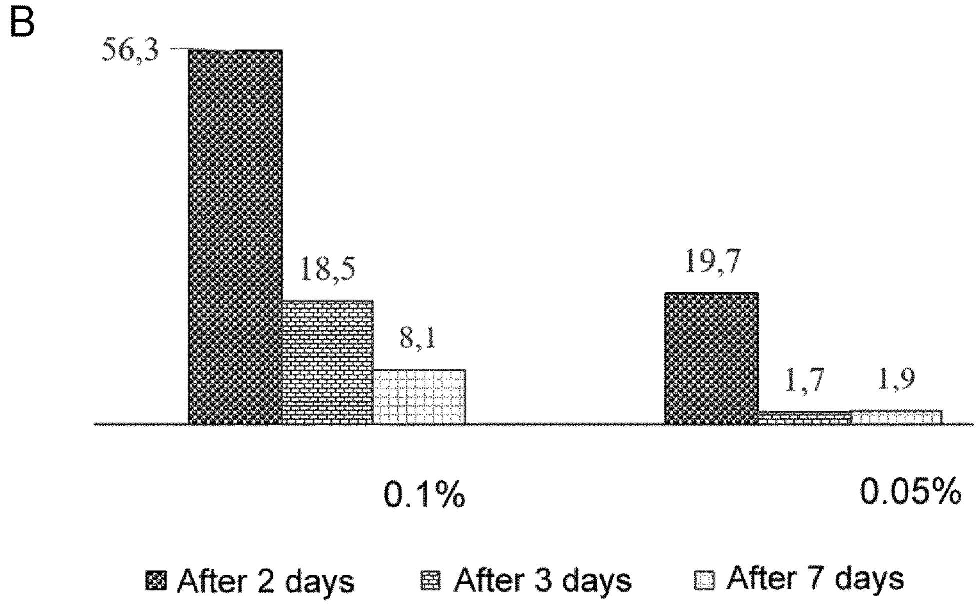
FIG. 6 represents the effects of a treatment with a cross-linked chitosan of the invention (at 0.1% w/w or 0.05% w/w in water) on germination process of Spring Wheat seeds in a germination chamber (A) (Radicle emergence was measured after 1 day, Germination energy was measured after 3 days; and germination capacity after 7 days) and on growth increase (% increase over control) of aerial parts of Spring Wheat seedlings in soil substrate (B) (seeds were treated 7 days prior to sowing.) as described in Example 6 compared to control.

A positive effect of the treatment with the cross-linked chitosan of the invention was demonstrated at the lowest concentration, as shown in FIG. 6 for germination and as summarized in Table 2 below for seedling development at the initial stages of organogenesis:

TABLE 2

| Growth duration | Growth indicators | A | B | C |
|---|---|---|---|---|
| 3 days | Number of roots per seedling | 2.9 | 3.0 | 3.0 |
| | Root length per seedling, cm | 7.79 ± 0.27 | 8.64 ± 0.46 | 10.20 ± 0.94 |
| | Length of individual root, cm | 2.60 ± 0.12 | 2.86 ± 0.08 | 3.4 ± 0.11 |
| | Length of shoot, cm | 1.84 ± 0.09 | 2.29 ± 0.03 | 2.69 ± 0.30 |
| 7 days | Number of roots per seedling | 4.41 | 4.68 | 4.83 |
| | Length of shoot, cm | 10.05 ± 0.75 | 10.11 ± 0.69 | 11.27 ± 0.26 |
| | air-dried biomass of roots, per seedling, mg | 8.20 ± 0.07 | 9.60 ± 0.56 | 9.40 ± 0.20 |
| | air-dried biomass of 1 root, mg | 1.86 ± 0.02 | 2.06 ± 0.15 | 1.95 ± 0.08 |
| | air-dried biomass of 1 seedling, mg | 15.13 ± 0.13 | 17.25 ± 0.19 | 16.45 ± 0.41 |

Higher rates of radicle emergence were observed within one day of cross-linked chitosan treatment. The strongest effect was observed with the low concentration suspension (22.9% increase with cross-linked chitosan 0.05%; 14.6%; increase with cross-linked chitosan 0.1%, with 75% baseline control). The same trend was observed when measuring germination energy (6.2% increase) and germination capacity (control=93.8%). Treating the seeds with the high concentration cross-linked chitosan suspension increased the germination capacity by 4.1%. In the early stages of organogenesis, cross-linked chitosan led to an increase in root growth. After 3 days, the total length of roots was 10.9% and 30.9% higher for the cross-linked chitosan 0.1% and cross-linked chitosan 0.05% groups, respectively (control=7.79 cm). At the same time, the most uniform increase was observed in the high concentration cross-linked chitosan group (cross-linked chitosan 0.1% coefficient of uniformity=81% (n=45); cross-linked chitosan 0, 05%=78.2% (n=48); control=68.9% (n=45)). The same trend was observed when measuring the height of the seedlings. If the increase after cross-linked chitosan 0.05% treatment (46.2% higher than the control=1.84 cm) was more significant than that after cross-linked chitosan 0.1% (24.4% higher than the control), the coefficient of uniformity was higher for the high concentration cross-linked chitosan-treated group (cross-linked chitosan 0.1%=75.4%; cross-linked chitosan 0.05%=72.8% control=61.7%).

Based on measurements made 7 days after the beginning of the experiment, the low concentration cross-linked chitosan treatment enhanced root formation the most (cross-linked chitosan 0.05%: increase of 9.5%; cross-linked chitosan 0.1%: increase of 6.1%, average number of roots in the control group: 4.41 per seedling). The same was found for the increase in overall seedling length (cross-linked chitosan 0.05%: increase of 7.7%; Control: 10.05 cm). In contrast, the highest increase in the biomass was observed following treatment with the more concentrated cross-linked chitosan suspension both for the roots (cross-linked chitosan 0.1%: increase of 17.1%; cross-linked chitosan 0.05%: increase of 14.6%) and for the entire seedling (cross-linked chitosan 0.1%: increase of 12.9%; cross-linked chitosan 0.05%: increase of 8.7%).

Assessment of the Effects on the Growth and Development of Seedlings of Spring Wheat in Soil Substrate Seeds were treated 7 days prior to sowing (alkaline chernozem, 500 gram per plastic pot/12 pots, repeated 4 times, natural lighting, t=20-22° C., controlled soil humidity). Germination energy, germination capacity, the height and biomass of seedlings were measured. Growth parameters were recorded during the first 7 days. A higher rate of radicle emergence was observed after 24 hours for seeds treated with cross-linked chitosan, especially for the higher concentration (control: 70.8%, relative increase for treated seeds: 27.1% and 23%). 100% germination was obtained after high concentration cross-linked chitosan treatment as shown under Table 3 below and under FIG. 6.

TABLE 3

| Indicators | | | Experimental groups A | B | C |
|---|---|---|---|---|---|
| Germination energy, % | After 1 day | Radicle emergence | 70.8 | 97.9 | 93.8 |
| | After 2 days | Normally germinated | 95.9 | 93.8 | 100 |
| | After 3 days | seedlings % | 97.9 | 100 | 83.4 |
| Germination, % | | After 7 days | 93.8 | 100 | 83.4 |
| Length of normally developed shoot, cm | | After 2 days | 0.71 ± 0.05 | 1.11 ± 0.05 | 0.85 ± 0.03 |
| | | After 3 days | 2.87 ± 0.13 | 3.40 ± 0.13 | 2.92 ± 0.06 |
| | | After 7 days | 18.95 ± 0.30 | 20.48 ± 0.24 | 19.31 ± 0.28 |
| air-dried biomass, mg | | Total seedling | 16.65 ± 0.32 | 18.95 ± 0.41 | 20.90 ± 0.37 |
| | | Roots, per seedling | 6.93 ± 0.14 | 8.53 ± 0.23 | 9.33 ± 0.22 |

The high initial rate of stimulation of growth resulting from 0.1% cross-linked chitosan treatment 56.3% after 2 days) was reduced 3-fold after 3 days (cross-linked chitosan, 0.05%, by 11.6 fold), and after 7 days, by 2.3 fold. The increase in biomass after 7 days compared to the control (16.63 mg) was higher in both the 0.1%-treated group (14% higher for total biomass and 23.8% for roots) and the 0.05%-treated group (25.7% higher for total biomass and 35.1% for roots). 0.05% cross-linked chitosan treatment led to a 1.8-fold increase in total biomass and 1.5-fold increase in root biomass.

Altogether, those data support that treatments with a cross-linked chitosan of the invention resulted in significant growth stimulation in germinating Spring Wheat.

The invention claimed is:

1. A method for the preparation of a cross-linked chitosan comprising the following steps:

a) providing a chitosan and leaving the said chitosan to swell in a solvent;

b) acylating-b) acylating the amino groups of said chitosan with an acrylic compound of Formula (I):

(I)

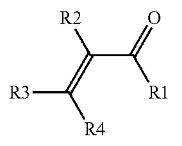

wherein $R_1$ is an a halogen or any other leaving group that upon removal, ensures acylation of an amino group; $R_2$, $R_3$ and $R_4$ are independently selected from H, optionally substituted $C_1$-$C_6$ alkyl, optionally substituted $C_2$-$C_6$ alkenyl, optionally substituted alkynyl, optionally substituted $C_3$-$C_8$-cycloalkyl, optionally substituted $C_4$-$C_8$ cycloalkenyl, optionally substituted $C_5$-$C_8$ cycloalkynyl, optionally substituted heterocycloalkyl, optionally substituted aryl, optionally substituted heteroaryl and optionally substituted aryl $C_1$-$C_6$ alkyl; wherein the term "substituted" refers to groups substituted with from 1 to 5 substituents selected from the group consisting of halogen, —COOR', —NR'R", =O, —OR', —COR', —CONR'R", —SR', —$SO_3$R', —$SO_2$NR'R", —SOR", —$SO_2$R', —$NO_2$, or —CN; or $R_1$ and $R_2$ or $R_1$ and $R_3$, or $R_1$ and $R_4$ together form 4-24 membered aryl, heteroaryl, cycloalkyl or heterocycloalkyl;

c) reacting the acylation product of step b) in the presence of a base, wherein step c) is carried out in an aprotic solvent or using the base as a solvent; and d) purifying the cross-linked chitosan obtained from step c).

2. The method according to claim 1, wherein said method further comprises a drying step e) of the product from step d).

3. The method according to claim 1, wherein $R_1$ is a halogen.

4. The method according to claim 1, wherein the acrylic compound is selected from acryloyl chloride and methacryloyl chloride.

5. The method according to claim 1, wherein said method further comprises a saponification step f) after step c) or step d) under alkaline conditions and the obtained product can be further subjected to at least one sequence of steps b) to c) or steps b) to d).

6. The method according to claim 1, wherein step a) and/or b) is carried out in a protic solvent and free acrylic acids formed after step b) are washed off before carrying out step c).

7. The method according to claim 1, wherein step a) and/or b) is carried out in the absence of water.

8. The method according to claim 1, wherein a solution of a biologically active material is added to the product resulting from step b) before conducting step c) to integrate the biologically active material within the obtained cross-linked chitosan.

9. The method according to claim 1, wherein $R_1$ is chloro.

10. The method according to claim 1, wherein the leaving group is selected from N-hydroxysuccinimide, pentachlorophenol, and a 2-nitro-4-sulfophenol ester.

11. A cross-linked chitosan obtainable by the method according to claim 1 or any pharmaceutically acceptable salts thereof.

12. A composition comprising at least one cross-linked chitosan according to claim 11 and at least one carrier.

13. The composition according to claim 12, wherein said composition is a pharmaceutical composition and the said carrier is a pharmaceutically acceptable carrier or is a cosmetic composition and the said carrier is a cosmetically acceptable carrier.

14. The composition according to claim 12, wherein said composition is a cell or tissue culture medium further comprising cell or tissue nutrients.

15. The composition according to claim 12, wherein said composition is a reconstruction tissue.

16. The composition according to claim 12, wherein said composition is an agricultural composition.

17. A soft tissue filler, a wound dressing or a reconstruction tissue comprising at least one cross-linked chitosan according to claim 11.

18. Nanoparticles comprising at least one cross-linked chitosan according to claim 11.

19. A culture medium for cells or biological tissue comprising at least one cross-linked chitosan according to claim 11.

20. A pharmaceutical formulation comprising the cross-linked chitosan according to claim 11 for use in the treatment of a disease or disorder selected from cardiac arrhythmias, atrial fibrillation and hypertension, joint pathologies and articular diseases, rheumatoid arthritis, osteoarthritis, spondyloarthritis, traumatic events leading to cartilage, bone, ligament or synovial capsule damage, eye pathologies and injuries, dry eye syndrome, uveitis, glaucoma, corneal lesions, connective tissue disorders, lupus and polymyositis, skin/mucous membrane disorders or injuries, wounds, scars, psoriasis, acne, eczema, rosacea, burns of physical or chemical nature, surgical wounds, sunburns, ulcers, haemorrhoids, periodontal and dental diseases, dural damage, malignant and benign neoplasms, carcinomas, sarcomas, lymphomas, melanomas, fistulas and infections, tumors or vascular malformations.

21. A method of preparation of a reconstruction tissue comprising a step of combining the cross-linked chitosan according to claim 11 with materials, tissues or cells useful for repairing damaged tissues of the body.

22. The method according to claim 21, wherein the tissues useful for repairing damaged tissues of the body comprise epidermal tissue, neurological tissue, cartilage or bone.

23. The method according to claim 21, wherein the cells useful for repairing damaged tissues of the body comprise stem cells.

* * * * *